US006641828B1

(12) United States Patent
Howarth et al.

(10) Patent No.: US 6,641,828 B1
(45) Date of Patent: *Nov. 4, 2003

(54) METHODS FOR MICROBIOLOGICAL CONTROL IN AQUEOUS SYSTEMS

(75) Inventors: Jonathan N. Howarth, Baton Rouge, LA (US); Christopher J. Nalepa, Baton Rouge, LA (US); Michael J. Sanders, Baton Rouge, LA (US)

(73) Assignee: Albemarle Corporation, Richmond, VA (US)

(*) Notice: Subject to any disclaimer, the term of this patent is extended or adjusted under 35 U.S.C. 154(b) by 33 days.

This patent is subject to a terminal disclaimer.

(21) Appl. No.: 09/775,516

(22) Filed: Feb. 2, 2001

Related U.S. Application Data

(63) Continuation-in-part of application No. 09/484,938, filed on Jan. 18, 2000.

(51) Int. Cl.$^7$ .............................................. A01N 25/10
(52) U.S. Cl. ........................ 424/405; 424/408; 424/420; 424/417; 514/389
(58) Field of Search .................................. 424/405, 406, 424/407, 408, 409, 417–420; 514/386, 389

(56) References Cited

U.S. PATENT DOCUMENTS

| | | | | |
|---|---|---|---|---|
| 2,130,805 A | | 9/1938 | Levine | 210/28 |
| 2,392,505 A | | 1/1946 | Rogers | 260/309.5 |
| 2,398,598 A | | 4/1946 | Rogers | 260/309.5 |
| 2,779,764 A | | 1/1957 | Paterson | 260/309.5 |
| 2,795,556 A | | 6/1957 | Quinn | 252/187 |
| 2,868,787 A | | 1/1959 | Paterson | 260/248 |
| 2,920,997 A | | 1/1960 | Wolf et al. | 167/33 |
| 2,971,959 A | | 2/1961 | Waugh et al. | 260/309.5 |
| 2,971,960 A | | 2/1961 | Waugh et al. | 260/309.5 |
| 3,121,715 A | | 2/1964 | Waugh et al. | 260/248 |
| 3,147,259 A | | 9/1964 | Paterson | 260/248 |
| 3,345,371 A | | 10/1967 | Paterson | 260/192 |
| 3,626,972 A | | 12/1971 | Lorenzen | 137/268 |
| 4,078,099 A | | 3/1978 | Mazzola | 427/213 |
| 4,119,535 A | * | 10/1978 | White et al. | 210/62 |
| 4,126,717 A | | 11/1978 | Mazzola | 427/220 |
| 4,136,052 A | | 1/1979 | Mazzola | 252/94 |
| 4,199,001 A | | 4/1980 | Kratz | 137/268 |
| 4,242,216 A | | 12/1980 | Daugherty et al. | 252/103 |
| 4,270,565 A | | 6/1981 | King, Sr. | 137/268 |
| 4,293,425 A | | 10/1981 | Price | 210/754 |
| 4,327,151 A | | 4/1982 | Mazzola | 428/407 |
| 4,331,174 A | | 5/1982 | King, Sr. | 137/268 |
| 4,427,692 A | | 1/1984 | Girard | 424/273 R |
| 4,465,839 A | | 8/1984 | Schulte et al. | 548/310 |
| 4,532,330 A | | 7/1985 | Cole | 548/311 |
| 4,537,697 A | | 8/1985 | Girard | 252/90 |
| 4,560,766 A | | 12/1985 | Girard et al. | 548/311 |
| 4,571,333 A | | 2/1986 | Hsiao et al. | 424/22 |
| 4,597,941 A | | 7/1986 | Bottom et al. | 422/37 |
| 4,621,096 A | | 11/1986 | Cole | 514/389 |

(List continued on next page.)

FOREIGN PATENT DOCUMENTS

| | | |
|---|---|---|
| CA | 1230825 | 12/1987 |
| CA | 2042430 | 11/1991 |
| CA | 2163596 | 9/1996 |
| EP | 0177645 | 4/1986 |
| EP | 0206725 | 12/1986 |
| EP | 0228593 | 7/1987 |
| EP | 0581826 | 9/1995 |
| GB | 1600289 | 10/1931 |
| GB | 1054243 | 1/1967 |
| GB | 1600289 | 10/1981 |
| GB | 2273106 | 6/1994 |
| JP | 56158333 | 12/1981 |
| JP | 7299468 | 11/1995 |
| WO | 8910696 | 11/1989 |
| WO | 9630491 | 10/1996 |
| WO | 9715652 | 5/1997 |
| WO | 9720546 | 6/1997 |
| WO | 9720909 | 6/1997 |
| WO | 9743264 | 11/1997 |
| WO | 9743392 | 11/1997 |
| WO | 0034186 | 6/2000 |

OTHER PUBLICATIONS

Gottarai: Reaction of Cl. BR—In Aqueous Solution (76 Zeutralbs. Bakteriol., Parasiteukd,) In Fektionskr. Hyg., Abt. 1; Orig., Geihe B 162 (3–4), 384–8.*
Corral et al., "Substitution in the Hydantoin Ring. III. Halogenation", J. Org. Chem., 1963, vol. 28, pp. 1100–1104.
Jolles, "General Methods of Bromination", Bromine and its Compounds, 1966, Ernest Benm, London, ppg. 365.
Markish et al., "New Aspects on the Preparation of 1,3–Dibromo–5,5–Dimethylhydantoin", Ind. Eng. Chem. Res. 1995, vol. 34, ppg. 2125–2127.

(List continued on next page.)

*Primary Examiner*—Neil S. Levy
(74) *Attorney, Agent, or Firm*—Edgar E. Spielman, Jr.

(57) ABSTRACT

Microbiological control in aqueous media and/or eradication or reduction of biofilm on a surface in contact with such media is achieved by introducing into the aqueous medium a microbiocidally effective quantity of one or more 1,3-dibromo-5,5-dialkylhydantoins where one of the alkyls is methyl and the other is a $C_{1-4}$ alkyl, wherein (i) the molar quantity of 1,3-dibromo-5,5-dialkylhydantoin introduced is less than the molar quantity of N,N'-bromochloro-5,5-dimethylhydantoin that would be required to effect the same degree of microbiological control in that medium, (ii) the molar quantity of the 1,3-dibromo-5,5-dialkylhydantoin introduced releases an amount of "free chlorine" that is greater than the amount of "free chlorine" that would be released in that medium by an equimolar quantity of N,N'-bromochloro-5,5-dimethylhydantoin, and (iii) the amount of "free chlorine" released by the quantity of the 1,3-dibromo-5,5-dialkylhydantoin introduced is greater than the amount of "free chlorine" that could be predicted to be released by that quantity of 1,3-dibromo-5,5-dialkylhydantoin on the basis of the amount of "free chlorine" that would be released in that medium by an equimolar quantity of N,N'-bromochloro-5,5-dimethylhydantoin.

27 Claims, 2 Drawing Sheets

U.S. PATENT DOCUMENTS

| | | | | |
|---|---|---|---|---|
| 4,654,424 A | 3/1987 | Girard et al. | ............... | 548/311 |
| 4,659,359 A | 4/1987 | Lorenz et al. | ................. | 71/67 |
| 4,662,387 A | 5/1987 | King, Sr. | .................... | 137/268 |
| 4,677,130 A | 6/1987 | Puzig | ......................... | 514/389 |
| 4,698,165 A | 10/1987 | Theyson | ..................... | 210/755 |
| 4,713,079 A | 12/1987 | Chun et al. | .................... | 8/101 |
| 4,728,453 A | 3/1988 | Choy | .......................... | 252/91 |
| 4,745,189 A | 5/1988 | Lee et al. | .................... | 544/221 |
| 4,780,197 A | 10/1988 | Schuman | .................... | 210/136 |
| 4,803,079 A | 2/1989 | Hsiao et al. | ................ | 424/468 |
| 4,867,895 A | 9/1989 | Choy | .......................... | 252/91 |
| 4,919,841 A | 4/1990 | Kamel et al. | .......... | 252/186.26 |
| 4,925,866 A | 5/1990 | Smith | ......................... | 514/389 |
| 5,076,215 A | 12/1991 | King | .......................... | 137/268 |
| 5,218,983 A | 6/1993 | King | ............................ | 137/1 |
| 5,338,461 A | 8/1994 | Jones | ........................ | 210/755 |
| 5,339,889 A | 8/1994 | Bigham | ........................ | 165/1 |
| 5,384,102 A | 1/1995 | Ferguson et al. | ........... | 422/264 |
| 5,422,126 A | 6/1995 | Howarth et al. | ............ | 424/723 |
| 5,476,116 A | 12/1995 | Price et al. | ................. | 137/268 |
| 5,565,105 A | 10/1996 | Sweeny | ...................... | 210/755 |
| 5,565,576 A | * 10/1996 | Hall | ....................... | 548/317.1 |
| 5,578,559 A | 11/1996 | Dolan et al. | ................ | 510/192 |
| 5,591,692 A | 1/1997 | Jones et al. | ................. | 504/124 |
| 5,603,941 A | 2/1997 | Farina et al. | .............. | 424/405 |
| 5,610,126 A | 3/1997 | Barford et al. | ............. | 510/191 |
| 5,614,528 A | 3/1997 | Jones et al. | ................. | 514/258 |
| 5,670,451 A | 9/1997 | Jones et al. | ................. | 504/134 |
| 5,750,061 A | 5/1998 | Farina et al. | .............. | 264/117 |
| 5,753,602 A | 5/1998 | Hung et al. | ................. | 510/192 |
| 5,756,440 A | 5/1998 | Watanabe et al. | ........... | 510/191 |
| 5,763,376 A | 6/1998 | Ward et al. | ................. | 510/191 |

OTHER PUBLICATIONS

Orazi et al., "Halogenacion con 3–Bromo–5,5–Dimetil–Hidantoina", Anales Assoc. Quim. Argetina, 1949, vol. 37, ppg. 192–196. (Not translated).

Orazi et al., "Halogenacion Con 1–3–Dibromo–5, 5–Dimetil–Hidantoina", Anales Assoc. Quim. Argentina, 1950, vol. 38, ppg. 5–11. (Not translated).

March, "Advanced Organic Chem.", 1992, 4$^{th}$ Edition, ppg. 639–640.

HCAPLUS Abstract of JP 07171576 A2 issued 1995.

HCAPLUS Abstract of JP 07277912 A2 issued 1995.

HCAPLUS Abstract of JP 08027119 A2 issued 1996.

Chowhan et al., "Hardness Increase Induced by Partial Moisture Loss in Compressed Tablets and Its Effect on In Vitro Dissolution", J. Pharm. Sciences, Oct. 1978, vol. 67, No. 10, ppg. 1385–1389.

Krycer et al., "An Evaluation of Tablet Binding Agents Part II. Pressure Binders", Powder Technology, 1983, vol. 34, ppg. 53–56.

Petterson, "N–Halogen Compounds. I. Decomposition of 1,3–Dichloro–5,5–dimethylhydantoin in Water at pH 9", J. Org. Chem., 1959, vol. 24, ppg. 1414–1419.

HCAPLUS Abstract of JP 08239699 A2 issued 1996.

HCAPLUS Abstract of JP 09087684 A2 issued 1997.

HCAPLUS Abstract of JP 09227317 A2 issued 1997.

Author unknown, "Big Brother Brominator—Brominators", Bulky Systems Website, <http://www.bulkysystems-inc.com/ brominator.html> (Visited Aug. 10, 2001). 1 page.

Author unknown, "Bio Lab Brominator", Conley Company Website, <http://www.conelyco.com/Pool–Spa/parts/bio-brom.htm> (Visited Aug. 10, 2001) 2 pages.

Hayward America's #1 Pool Water Systems Product Catalog, "Automatic Chemical Feeders" Chlorinators (Slow Dissolve Tri–Chlor Only) and Brominators, Hayward Pool Products Inc. Website, <http://www.haywardnet.com/products/catalog/displayProdInfo.cfm?itemID=61>, 2 pages.

Hayward Pool Products Owner's Guide, Installation and Operating Instructions, "Hayward Chemical Feeder", Models C250CF, C500CF, C1100CF, C1800CF, C2400CF,— 1998—4 pages.

Hayward America's #1 Pool Water Systems Product Catalog, "Automatic Chemical Feeders" Chlorinators (Slow Dissolve Tri–Chlor Only) and Brominators, Buyers Guide, Hayward Pool Products Inc., Website, <http://www.haywardnet.com/products/catalog/displayProdInfo.cfm? item ID= 60>, 2 pg..

Pentair Pool Products Brochure, "Rainbow High Capacity Chlorine/Bromine Feeders", "Unsurpassed Performance From The Industry's Leader in Automatic Sanitizing of Large Residential and Commercial Pools", date unknown, 1 page.

Pentair Pool Products Brochure, "Rainbow Model 320 Automatic Chlorine/Bromine In–line Feeder", "Saves Time, Reduces Manual Handling of Chemicals", date unknown, 7 pages '99.

Sani–King Perform–Max Pool Sanitizer Instruction Guide, Models 910, 940, & 980 (Inline) and Models 930 & 960 (Off–line), date unknown, 16 pages, Prior to Jan. 18, 2000.

Sani–King Spa Feeder Product Brochure Model 740 from King Technology Website, <http://www.king-technology.com/ spafeeder.htm> Visited (Aug. 10, 2001), 2000, 4 pages.

Sani–King Adjust–A–Flo Product Brochure from King Technology Website<http://www.kingtechnology.com/spafeeder.htm> (Visited Aug. 10, 2001), 2000, 1 page.

Sani–King Perform–Max Sanitizers for Inground Pools Product Brochure for Model 940 & 960 from King Technology Website, <http://www.kingtechnology.com/perfermaxIG.htm>, visited Aug. 10, 2001, 2000, 1 page.

Sani–King Perform–Max Sanitizers for Above Ground Pools Products Model 910 & 930 from King Technology Website, <http://www.kingtechnology.com/perfemaxIG.htm>, visited Aug. 10, 2001, 2000, 1 page.

Discount Pool & Spa Supplies Automatic Chlorinators and Chemical Feeders Website, <http://www.discountpoolsupplies.com/Chemfeeders/> Visited Aug. 10, 2001, 3 pages.

Author unknown, "Big Brother Brominator—Brominators", Bulky Systems Website, <http://www.bulkysystems-inc.com/ brominator.html> (Visited Aug. 10, 2001). 1 page.

Author unknown, "Bio Lab Brominator", Conely Company Website, <http://www.conelyco.com/Pool–Spa/parts/bio-brom.htm> (Visited Aug. 10, 2001) 2 pages.

Hayward America's #1 Pool Water Systems Product Catalog, "Automatic Chemical Feeders" Chlorinators (Slow Dissolve Tri–Chlor Only) and 1 and Brominators, Hayward Pool Products Inc. Website, <http://www.haywardnet.com/products/catalog/displayProdInfo.cfm?itemID=61>, 2 pages.

Hayward Pool Products Owner's Guide, Installation and Operating Instructions, "Hayward Chemical Feeder", Models C250CF, C500CF, C1100CF, C1800CF, C2400CF,— 1998—4 pages.

Hayward America's #1 Pool Water Systems Product Catalog, "Automatic Chemical Feeders" Chlorinators (Slow Dissolve Tri–Chlor Only) and 2001 Brominators, Buyers Guide, Hayward Pool Products Inc., Website, <http://www.haywardnetcom/products/catalog/display ProInfo.cfm?itemID=60>,2 pg.

Discount Pool & Spa Supplies, Automatic Chlorinators and Chemical Feeders Website, <http://www.discountpoolsupplies.com/Chemfeeders/> Visited Aug. 10, 2001, 3 pages.

Pentair Pool Products Brochure, "Rainbow Model 320 Automatic Chlorine/Bromine In–line Feeder", "Saves Time, Reduces Manual Handling of Chemicals", 7 pages, '99.

Sani–King Spa Feeder Product Brochure Model 740 from King Technology Website, <http://www.kingtechnology.com/ spafeeder.htm> Visited (Aug. 10, 2001), 2000, 4 pages.

Sani–King Adjust–A–Flo Product Brochure from King Technology Website <http://www.kingtechnology.com/spafeeder.htm> (Visited Aug. 10, 2001), 2000, 1 page.

Sani–King Perform–Max Sanitizers for Above Ground Pools Product Borchure Model 910 & 930 from King Technology Website, <http://www.kingtechnology.com/perfermaxIG.htm>, visited Aug. 10, 2001, w000, 1 page.

Discount Pool & Spa Supplies, Automatic Chlorinators and Chemical Feeders Website, <http://www.discountpoolsupplies.com/Chemfeeders/> Visited Aug. 10, 2001, 3 pages.

Sani–King Perform–Max Sanitizers for Inground Pools Product Brochure for Model 940 & 960 from King Technology Website, <http://www.kingtechnology.com/perfermaxIG.htm>, visited Aug. 10, 2001, 2000, 1 page.

* cited by examiner

METHODS FOR MICROBIOLOGICAL CONTROL IN AQUEOUS SYSTEMS

REFERENCE TO RELATED APPLICATION

This is a continuation-in-part of commonly-owned copending application Ser. No. 09/484,938, filed Jan. 18, 2000.

REFERENCE TO OTHER COMMONLY-OWNED APPLICATIONS

Commonly-owned copending application Ser. No. 09/484,844, filed Jan. 18, 2000, describes and claims chemical processes from which compositions of the present invention can be formed or derived. Commonly-owned copending application Ser. No. 09/484,687, filed Jan. 18, 2000, describes and claims 1,3-dibromo-5,5-dimethylhydantoin particulate solids producible by the processes of application Ser. No. 09/484,844, such solids having unprecedented enhanced properties, and compacted articles made from such particulate solids without use of a binder. Commonly-owned copending application Ser. No. 09/487,816, filed Jan. 18, 2000, relates in part to converting 1,3-dihalo-5,5-dimethylhydantoins into compacted articles using novel binders. Commonly-owned copending application Ser. No. 09/484,891, filed Jan. 18, 2000, relates to the compacting of 1,3-dihalo-5,5-dimethylhydantoins other than 1,3-dibromo-5,5-dimethylhydantoin without use of binders, and to the novel compacted forms so produced. Commonly-owned copending application Ser. No. 09/483,896, filed Jan. 18, 2000, relates to the granulation of small average particle size 1,3-dibromo-5,5-dimethylhydantoin and also to the compaction of such granulated products to form larger-sized articles.

BACKGROUND

As is known in the art of water treatment for microbiological control, a deficiency of chlorine, of hypochlorites, and of certain halogenated organic water-treating agents is the formation, during usage, of undesirable disinfection by-products. These by-products are undesirable both from the standpoint of environmental concerns and also from the standpoint of toxicological considerations.

Certain 1,3-dihalo-5,5-dialkylhydantoins have been found to be effective as biocides for aqueous systems such as industrial cooling water, recreational water, and wastewater.

Persons using biocidal agents in the biocidal treatment of water customarily, if not universally, refer to "free chlorine" level as a measure of biocidal control. To achieve "free chlorine" levels in water treatment, solid materials are often preferred because of their high weight percent activity. N,N'-bromochloro-5,5-dimethylhydantion (BCDMH) has been one of the most widely-used solid sources of "free chlorine" for water treatment. One of the features emphasized for BCDMH by suppliers of BCDMH is that in use, the combined chlorine from the biocide regenerates "free chlorine" by reaction with inactive bromide species formed during the water treatment operation. In other words, the chlorine atom in the initial N,N'-bromochloro-5,5-dialkylhydantoin is said to be a precursor for additional "free chlorine" for sanitation purposes.

In use, BCDMH hydrolyzes into HOBr and HOCl both of which register as "free chlorine" species in commonly-used standard test procedures. These methods for determining "free chlorine" levels in treated water, involve use of a reagent known as DPD (i.e., N,N'-diethyldiphenylenediamine) and a buffer, and the results of such analyses are commonly used, if not universally used, as the basis for determining the quantity of a halogen-containing microbiocidal agent to be used for water treatment. Heretofore, consumers of BCDMH have only been concerned with the level of "free chlorine" provided by a given quantity of that biocidal material. What has not been realized by such consumers is the amount of "total chlorine" being utilized in order to achieve the requisite "free chlorine" level. As a consequence, the consumer has not had available a yardstick by which to determine the true economic efficiency of using BCDMH as a biocidal agent in the treatment of water. To achieve optimum economic efficiency, the consumer should have available for use a biocidal agent in which the amount of "free chlorine" released into the water corresponds closely to the "total chlorine" content of the biocidal agent.

In the event a biocidal agent provides a relatively small amount of "free chlorine" in relation to its "total chlorine" content, it has been deemed necessary to utilize a relatively large amount of such agent in order to achieve microbiological control. This in turn means high levels of halogenated materials are released into the environment. If on the other hand, a biocidal agent could provide to the water an amount of "free chlorine" that closely corresponds to the "total chlorine" content of the biocidal agent, effective microbiological control could be realized by use of much smaller dosages and with consequent minimal adverse impact upon the environment.

BRIEF SUMMARY OF THE INVENTION

This invention involves, inter alia, the discovery that there is a substantial disparity between the "free chlorine" level and the "total chlorine" level delivered to the water when using BCDMH as a biocidal agent. Thus the consumer of BCDMH as a water treating agent unknowingly has been paying for a relatively ineffective microbiocidal agent. Moreover, such consumer has been contributing unknowingly to the release of undesirable quantities of halogenated materials to the environment.

This invention further involves, inter alia, the discovery that the level of "free chlorine" available from 1,3-dibromo-5,5-dimethylhydantoin (DBDMH), especially when used in water having a pH of at least about 8.0, closely approximates its "total chlorine" content. Consequently the use of one or more water-soluble dialkyldibromohydantoins such as DBDMH as a water treating agent, especially when used in the treatment of industrial cooling water, is highly effective from an economic standpoint and highly desirable from an environmental standpoint. That is to say, the dosage levels of water-soluble dialkyldibromohydantoins such as DBDMH needed to provide effective microbiological control with respect to such undesirable organisms and pathogens as bacteria, algae, and biofilms, are relatively low compared to dosage levels of BCDMH required for the same degree of control, especially in industrial cooling water. Moreover, the levels of halogenated materials released to the environment are much smaller when using a water-soluble dialkyldibromohydantoin such as DBDMH as compared to BCDMH.

Accordingly, this invention provides in one of its embodiments a method of providing microbiological control in an aqueous medium such as recreational water, industrial cooling water, process water, or wastewater, and preferably in water having a pH of at least about 8.0 such as cooling water and/or eradication or reduction of biofilm on a surface in contact with such aqueous medium, which method comprises introducing into the aqueous medium a microbiocidally effective amount of at least one 1,3-dibromo-5,5-dialkylhydantoin in which one of the alkyl groups in the 5-position is a methyl group and the other alkyl group in the 5-position contains in the range of 1 to 4 carbon atoms (DBDAH), (i) the molar quantity of the DBDAH introduced being less than the molar quantity of N,N'-bromochloro-5,5-dimethylhydantoin (BCDMH) that would be required to effect the same degree of microbiological control in such medium, (ii) the quantity of DBDAH introduced into such aqueous medium releasing an amount of "free chlorine" that is greater than the amount of "free chlorine" that would be released in such medium by an equimolar quantity of BCDMH, and (iii) the amount of "free chlorine" released by the quantity of such at least one DBDAH introduced into such aqueous medium being greater than the amount of "free chlorine" that could be predicted to be released by that quantity of DBDAH on the basis of the amount of "free chlorine" that would be released in such medium by an equimolar quantity of BCDMH. The most preferred DBDAH used in this embodiment is 1,3-dibromo-5,5-dimethylhydantoin (DBDMH).

In another of its embodiments this invention provides a method of effecting microbiocidal activity in water preferably but not necessarily having a pH of at least about 8.0, which method comprises providing in such water using a 1,3-dibromo-5,5-dialkylhydantoin (DBDAH) microbiocidal agent in which one of the alkyl groups of the DBDAH in the 5-position is a methyl group and the other alkyl group in the 5-position contains in the range of 1 to 4 carbon atoms, a microbiocidally effective amount of "free chlorine" that is greater than could be predicted from the amount of "free chlorine" that would be released by an equimolar quantity of N,N'-bromochloro-5,5-dimethylhydantoin (BCDMH) in such water, while using a smaller molar quantity of the DBDAH than the molar quantity of BCDMH required to release such microbiocidally effective amount of "free chlorine". 1,3-Dibromo-5,5-dimethylhydantoin (DBDMH) is also the most preferred microbiocidal agent employed in this embodiment.

A further embodiment of this invention is a composition having microbiocidal activity, which composition comprises water preferably but not necessarily having a pH of at least about 8.0 to which has been added a microbiocidally effective quantity of a 1,3-dibromo-5,5-dialkylhydantoin (DBDAH) in which one of the alkyl groups is a methyl group and the other alkyl group contains in the range of 1 to 4 carbon atoms, (i) the molar quantity of the DBDAH added being less than the molar quantity of N,N'-bromochloro-5,5-dimethylhydantoin (BCDMH) that would be required to effect the same degree of microbiocidal activity in that water, (ii) the quantity of DBDAH added releasing an amount of "free chlorine" that is greater than the amount of "free chlorine" that would be released in that water by an equimolar quantity of BCDMH, and (iii) the amount of "free chlorine" released by the amount of DBDAH added being greater than the amount of "free chlorine" that could be predicted to be released by DBDAH on the basis of the amount of "free chlorine" that would be released in that water by an equimolar quantity of BCDMH. Here again, the most preferred DBDAH is 1,3-dibromo-5,5-dimethylhydantoin (DBDMH).

This invention as reflected for example by the above embodiments, involves a number of surprising features. First of all, it is surprising that to achieve a given level of microbiocidal effectiveness, especially in an aqueous medium with a pH of at least about 8.0, a smaller quantity of DBDAH such as DBDMH can be used than BCDMH. Heretofore the art has regarded BCDMH as being a biocidal agent of choice because of the levels of effectiveness achieved by use of that agent. Moreover, it is surprising that in an aqueous medium preferably but not necessarily with a pH of about 8.0 or higher, the amount of "free chlorine" released by a DBDAH such as DBDMH is greater than the amount of "free chlorine" released by an equimolar quantity of BCDMH. At best the expectation would be that there could be no significant difference, and thus that there would be no appreciable difference, in these respective amounts of "free chlorine". Furthermore, not until comparative testing of water samples with a pH of greater than about 8.0 containing, respectively, equimolar quantities of DBDMH or BCDMH for "free chlorine" using Hach Method 8021 (copyright 1997, by Hach Company) and for "total chlorine" using Hach Method 8167 (copyright 1997, by Hach Company), and converting the mg/L $Cl_2$ "free chlorine" values from the tests to percentages of the mg/L $Cl_2$ "total chlorine" values from the tests, was the unpredictable superiority of DBDMH in releasing larger amounts of "free chlorine" than the equimolar quantity of BCDMH discovered. Prior to such testing there was no way of predicting the existence this superiority.

As a consequence of the above surprising features of this invention it is now possible to achieve the same microbiocidal effect on or control of bacteria, algae, biofilm, and like microbiological entities as given by BCDMH but using smaller molar amounts of one or more of the above described 1,3-dibromo-5,5-dialkylhydantoins such as DBDMH, and at the same time significantly reducing the amounts of halogenated materials to be released to the environment. Alternatively, greater microbiocidal control of bacteria, algae, biofilm, and like microbiological entities can be achieved using one or more of the above described 1,3-dibromo-5,5-dialkylhydantoins such as DBDMH in the same molar quantity as BCDMH, or even somewhat less molar quantity of one or more such 1,3-dibromo-5,5-dialkylhydantoins than BCDMH.

Another embodiment of this invention is a method for determining a quantity of a 1,3-dibromo-5,5-dialkylhydantoin such as DBDMH to be used in microbiocidal treatment of water preferably but not necessarily having a pH of at least about 8.0. The method comprises (i) determining the "free chlorine" concentrations of samples of said water containing respectively BCDMH and the DBDAH, (ii) determining the "total chlorine" values of samples of said water containing respectively BCDMH and DBDAH, and (iii) determining respectively for BCDMH and DBDAH the relative extent of hydrolysis to species which register as "free chlorine". Such determinations can be accomplished by dividing the value obtained for "free chlorine" by the value obtained for "total chlorine" and multiplying the quotient by 100 to obtain the percentage of hydrolysis to "free chlorine". Use of this method enables the amount of DBDAH to be used in achieving the target dose of "free chlorine". By "target dose" is meant the dose deemed suitable by the water treater to effect microbiocidal control in the water being subjected to treatment. In conducting this embodiment of the invention, any suitable method of determining "free chlorine" and "total chlorine" can be used, but in the event of any conflicting data as between different parties, Hach Method 8021 (copyright 1997) for "free chlorine" and Hach Method 8167 (copyright 1997) for "total chlorine" shall be used. For example, a given water treater may deem a slug dose of, say, 0.2 mg/L of "free chlorine" to be sufficient for maintaining microbiocidal control in a given body of water. Knowing the extent of hydrolysis as determined by use of this invention, and also the total volume of the body of water, the water treater can determine an amount of solid DBDAH to apply in a slug dose to achieve effective microbiocidal control while at the same time without using an undue excess of DBDAH.

In another of its embodiments, this invention provides a method of effecting biocidal activity in water preferably but not necessarily having a pH of at least about 8.0, which method comprises providing in such water using a 1,3-dibromo-5,5-dialkylhydantoin (DBDAH) biocidal agent an amount of "free chlorine" that is greater than could be predicted from the amount of "free chlorine" provided by an equimolar amount of N,N'-bromochloro-5,5-dimethylhydantoin (BCDMH), as determinable by comparative testing as follows:
   a) determining the amount of species of the DBDAH and of BCDMH which register respectively as "total chlorine" using Hach Method 8167 (copyright 1997, by Hach Company);
   b) determining the amount of species of the DBDAH and of BCDMH which register respectively as "free chlorine" using Hach Method 8021 (copyright 1997, by Hach Company); and
   c) determining respectively for the DBDAH and BCDMH the relative extent of hydrolysis to species which register as "free chlorine".

The foregoing method can be applied for treating water for microbiological control and/or for biofilm eradication.

Another embodiment is water preferably but not necessarily having a pH of at least about 8.0 in which microbiological and/or biofilm activity is minimized if not eliminated by the addition thereto of an amount of "free chlorine" using an above-described 1,3-dibromo-5,5-dialkylhydantoin (DBDAH) biocidal agent where the amount of "free chlorine" actually present in the water is greater than could be predicted from the amount of "free chlorine" provided by an equimolar amount of N,N'-bromochloro-5,5-dimethylhydantoin (BCDMH), as determinable by comparative testing as follows:
   a) determining the amount of species of the DBDAH and of BCDMH which register respectively as "total chlorine" using Hach Method 8167 (copyright 1997, by Hach Company); and
   b) determining the amount of species of the DBDAH and of BCDMH which register respectively as "free chlorine" using Hach Method 8021 (copyright 1997, by Hach Company); and
   c) determining respectively for the DBDAH and BCDMH the relative extent of hydrolysis to species which register as "free chlorine".

The microbiological control and/or for biofilm eradication in the water involves effective biocidal activity against such organisms and pathogens as bacteria, algae, and biofilms.

Other embodiments, features, and advantages of this invention will be still further apparent from the ensuing description and appended claims.

FURTHER DETAILED DESCRIPTION

Figure 1:
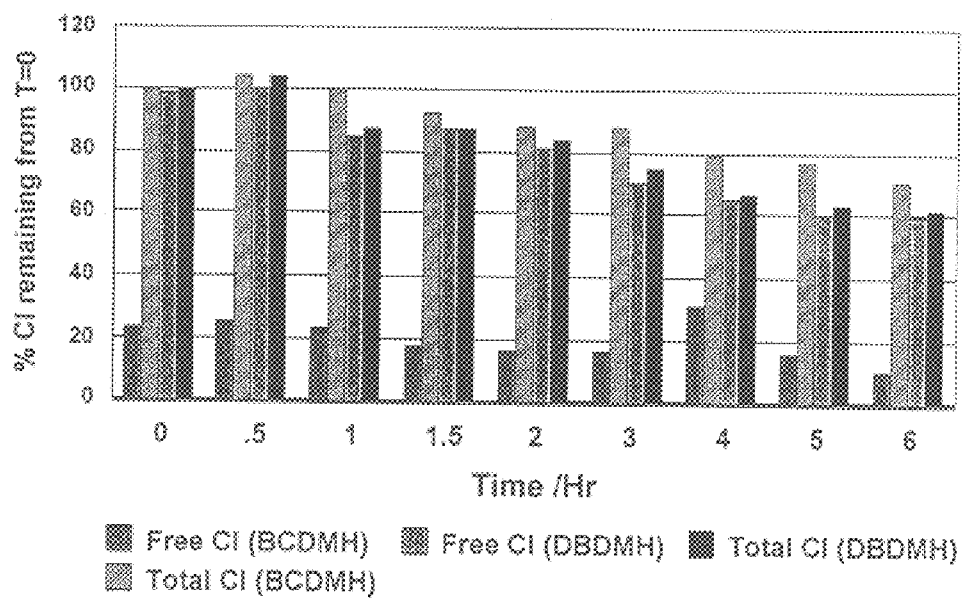
FIG. 1 is a graphical representation of the results of standard "free chlorine" and "total chlorine" tests performed on simulated cooling water solutions dosed with BCDMH or DBDMH, all as described in detail in Example 1 hereinafter.

At the outset it should be understood that the terms "free chlorine" and "total chlorine" are terms commonly used by persons in the fields of industrial and recreational water treatment. The values for the levels of "free chlorine" and "total chlorine" in the water are determined by use of appropriate standard test procedures which differentiate between the two. Further, the terms "free chlorine" and "total chlorine" are not restricted to just chlorine species in the water but rather, include certain bromine species in the water as well. Thus in a case where a biocidal agent used in treating the water contains both bromine and chlorine atoms (e.g., BCDMH), the "free chlorine" and "total chlorine" levels determined in the respective appropriate test procedures used would include quantification of the sum of the bromine species and chlorine species present that respond to the respective tests. The sum of these respective levels is reported, however, as "free chlorine" or "total chlorine", depending on the test used. Similarly, if the water treating agent used contains bromine atoms but no chlorine atoms, the "free chlorine" and "total chlorine" levels determined in the respective appropriate standard test procedures used would involve quantification of the level of bromine species present that respond to the respective tests. Thus although the halogen species actually present in such case are bromine-containing species, the levels present as determined in the respective tests would be reported as "free chlorine" and "total chlorine", respectively.

Heretofore it has been universally believed that all bromine species dissolved in the water respond positively in the standard "free chlorine" test procedure. However, one of the features of this invention is the discovery that this universal belief is erroneous when the "free chlorine" test procedure is applied to recreational water, cooling water, process water, and wastewater, that contains bromine species, and especially to cooling water, process water, and wastewater that is has a pH above about 8.0. Under these conditions the dibromo-containing microbiocides used pursuant to this invention can give vastly superior values for "free chlorine" as compared to the corresponding bromochloro microbiocides as evidenced by the results described herein in which comparisons were made between DBDMH and BCDMH.

For example, it has been found that when water having a pH above about 8.0 is treated water with BCDMH to reach a desired "free chlorine" level, the amount of BCDMH being used is far greater than necessary to achieve a given level of microbiocidal effectiveness. This in turn means that the consumer has purchased and is using much more of the microbiocidal agent than necessary. As a consequence, there are involved both an economic penalty due to excessive consumption, and an environmental penalty due to release of excessive quantities of less biocidally-active halogen species to the environment.

Nevertheless, the "free chlorine" level in water treated with a halogen-releasing biocidal agent remains the yardstick by which microbiocidal performance is measured. Species which respond to the standard "free chlorine" test are HOCl and HOBr. Any other form of soluble halogen species do not respond to the standard "free chlorine" test. Such non-responsive species include, for example, chlorine species bound to a nitrogen atom. On the other hand, the standard "total chlorine" test measures both HOBr and HOCl, and any halogen species that do not respond to the standard "free chlorine " test.

The standard tests for determination of "free chlorine" and "total chlorine" are based on classical test procedures devised by Palin in 1974. See A. T. Palin, "Analytical Control of Water Disinfection With Special Reference to Differential DPD Methods For Chlorine, Chlorine Dioxide, Bromine, Iodine and Ozone", *J. Inst. Water Eng.*, 1974, 28, 139. While there are various modernized versions of the Palin procedures, the version of the tests for "free chlorine" and "total chlorine" used and to be used as the standard in connection with this invention, are fully described in *Hach Water analysis Handbook*, 3rd edition, copyright 1997. The procedure for "free chlorine" is identified in that publication as Method 8021 appearing on page 335, whereas the procedure for "total chlorine" is Method 8167 appearing at page 379. Briefly, the "free chlorine" test involves introducing to the halogenated water a powder comprising DPD indicator powder and a buffer. "Free chlorine" present in the water reacts with the DPD indicator to produce a red to pink coloration. The intensity of the coloration depends upon the concentration of "free chlorine" species present in the sample. This intensity is measured by a calorimeter calibrated to transform the intensity reading into a "free chlorine" value in terms of mg/L $Cl_2$. Similarly, the "total chlorine" test also involves use of DPD indicator and buffer. In this case, KI is present with the DPD and buffer whereby the halogen species present, including nitrogen-combined halogen, reacts with KI to yield iodine species which turn the DPD indicator to red/pink. The intensity of this coloration depends upon the sum of the "free chlorine" species and all other halogen species present in the sample. Consequently, this coloration is transformed by the colorimeter into a "total chlorine" value expressed as mg/L $Cl_2$.

A halogen water treating agent which could provide a high level of both "free chlorine" and "total chlorine" and where these levels would be close together would be a very desirable water treating agent. Such an agent would be highly effective as a microbiocidal agent and if of an appropriate chemical structure, could be environmentally friendly and highly cost-effective. Pursuant to this invention these criteria are met by certain water-soluble 1,3-dibromo-5,5-dialkylhydantoins (DBDAH).

In particular, the water-soluble 1,3-dibromo-5,5-dialkylhydantoins utilized in the practice of this invention are those in which one of the alkyl groups in the 5-position is a methyl group and the other alkyl group in the 5-position is an alkyl group having in the range of 1 to 4 carbon atoms. Thus the biocides used in this invention comprise 1,3-dibromo-5,5-dimethylhydantoin, 1,3-dibromo-5-ethyl-5-methylhydantoin, 1,3-dibromo-5-n-propyl-5-methylhydantoin, 1,3-dibromo-5-isopropyl-5-methylhydantoin, 1,3-dibromo-5-n-butyl-5-methylhydantoin, 1,3-dibromo-5-isobutyl-5-methylhydantoin, 1,3-dibromo-5-sec-butyl-5-methylhydantoin, 1,3-dibromo-5-tert-butyl-5-methylhydantoin, and mixtures of any two or more of them. Of these biocidal agents, 1,3-dibromo-5-isobutyl-5-methylhydantoin, 1,3-dibromo-5-n-propyl-5-methylhydantoin, and 1,3-dibromo-5-ethyl-5-methylhydantoin are, respectively, preferred, more preferred, and even more preferred members of this group from the cost effectiveness standpoint. Of the mixtures of the foregoing biocides that can be used pursuant to this invention, it is preferred to use 1,3-dibromo-5,5-dimethylhydantoin as one of the components, with a mixture of 1,3-dibromo-5,5-dimethylhydantoin and 1,3-dibromo-5-ethyl-5-methylhydantoin being particularly preferred. The most preferred biocide employed in the practice of this invention is 1,3-dibromo-5,5-dimethylhydantoin.

When a mixture of two or more of the foregoing biocides is made up or used pursuant to this invention, the individual biocides of the mixture can be in any proportions relative to each other.

It is to be understood that in the practice of this invention it is not necessary to perform the specified tests every time a body of water is to be dosed with DBDAH or with BCDMH (depending upon the embodiment of this invention being practiced). Instead, as made clear by the use of the term "determinable" (i.e., able to be determined), the testing should be done when deemed necessary or desirable to either establish the requisite dosage of DBDAH or BCDMH, as the case may be, or to check or confirm that the proposed dosage complies with this invention and thus will make available the economic and environmental benefits resulting from the practice of this invention.

When it is desired to conduct the appropriate testing any suitable method of determining "free chlorine" and "total chlorine" can be used, but in the event of any conflicting data or dispute as between different parties, the full procedure set forth below entitled "DBDAH and BCDMH Test Procedure" is to be used to resolve the issue in connection with any embodiment of this invention.

DBDAH and BCDMH Test Procedure

1. To determine the amount of species present in the water which respond to the "free chlorine" and "total chlorine" tests, the water sample should be analyzed within a few minutes of being taken, and preferably immediately upon being taken.

2. Hach Method 8021 for testing the amount of species present in the water sample which respond to the "free chlorine" test involves use of the Hach Model DR 2010 calorimeter. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. Using the 10 mL cell riser, this is admitted to the sample compartment of the Hach Model DR 2010, and the shield is closed to prevent stray light effects. Then the ZERO key is depressed. After a few seconds, the display registers 0.00 mg/L $Cl_2$. To second cell, the contents of a DPD Free Chlorine Powder Pillow are added. This is shaken for 10–20 seconds to mix, as the development of a pink-red color indicates the presence of species in the water which respond positively to the DPD test reagent. Within one minute of adding the DPD "free chlorine" reagent to the 10 mL of water in the sample cell, the blank cell used to zero the instrument is removed from the cell compartment of the Hach Model DR 2010 and replaced with the test sample to which the DPD "free chlorine" test reagent was added. The light shield is then closed as was done for the blank, and the READ key is depressed. The result, in mg/L $Cl_2$ is shown on the display within a few seconds. This is the "free chlorine" level of the water sample under investigation. Hach Method 8167 for testing the amount of species present in the water sample which respond to the "total chlorine" test involves use of the Hach Model DR 2010 calorimeter. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. To the second cell, the contents of a DPD Total Chlorine Powder Pillow are added. This is shaken for 10–20 seconds to mix, as the development of a pink-red color indicates the presence of species in the water which respond positively to the DPD "total chlorine" test reagent. On the keypad, the SHIFT TIMER keys are depressed to commence a three minute reaction time. After three minutes the instrument beeps to signal the reaction is complete. Using the 10 mL cell riser, the blank sample cell is admitted to the sample compartment of the Hach Model DR 2010, and the shield is closed to prevent stray light effects. Then the ZERO key is depressed. After a few seconds, the display registers 0.00 mg/L $Cl_2$. Then, the blank sample cell used to zero the instrument is removed from the cell compartment of the Hach Model DR 2010 and replaced with the test sample to which the DPD "total chlorine" test reagent was added. The light shield is then closed as was done for the blank, and the READ key is depressed. The result, in mg/L $Cl_2$ is shown on the display within a few seconds. This is the "total chlorine" level of the water sample under investigation.

The various new features of this invention and the advantages accruing therefrom will be further apparent from Examples 1–3, which as presented for purposes of illustrating the invention without limiting the scope of the invention.

EXAMPLE 1

Simulated cooling water was prepared using deionized water to which calcium chloride and sodium bicarbonate were added to provide calcium hardness of 400 ppm and a total alkalinity of 300 ppm. A small amount of phosphonobutanetricarboxylic acid (PBTC) (5 ppm) was used to prevent calcium carbonate precipitation. Concentrated sodium hydroxide was added to adjust the pH of the simulated cooling water solutions to pH 9.1.

Stock solutions of DBDMH and of BCDMH were prepared by slurrying 1 gram of the respective powders in 100 mL of deionized water. After stirring for 20 minutes, the insolubles were filtered to yield clear saturated stock solutions of DBDMH and BCDMH, respectively. Iodometric titration of the stock solutions using the potassium iodide-sodium thiosulfate method indicated the DBDMH solution contained 580 mg/L (as total chlorine), and the BCDMH solution contained 1100 mg/L (as total chlorine).

The stock solutions were used to dose two simulated cooling water solutions to 1 mg/L as total chlorine. Thus, 1.7 mL of DBDMH stock solution was introduced to 1000 mL of simulated cooling water to form a first test solution, and 0.91 mL of BCDMH stock solution was introduced to another 1000 mL of simulated cooling water to produce a second test solution. Both of these test solutions were placed in screw-capped amber bottles to shield from light and prevent evaporation. The bottles were then placed in an oven and heated to 38° C. (100° F.). As soon as the solutions reached the equilibrium temperature of 38° C., 10 mL aliquots of each test solution were removed and analyzed using Hach Method 8167 for "total chlorine", to confirm that each contained a "total chlorine" level of 1 mg/L. The same solutions were also analyzed using Hach Method 8021 for "free chlorine" to determine how much of the total chlorine species also registered as "free chlorine". These analyses were recorded as results at time 0. The test solutions were then kept in the oven at the equilibrium temperature of 38° C. for a total of 6 hours during which time additional 10 mL aliquots were removed at known time intervals and subjected to the same analysis procedures for "free chlorine" and "total chlorine".

Figure 2:
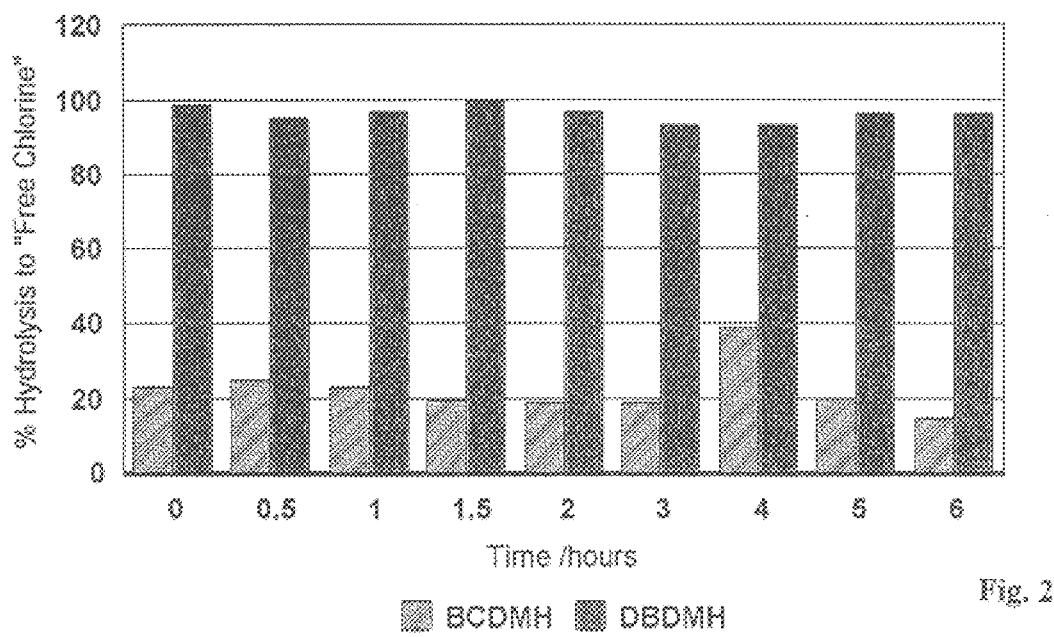
FIG. 2 is a graphical representation of the percent of hydrolysis experienced by the respective test samples of BCDMH and of DBDMH in the tests performed in Example 1.

The results of each of the foregoing determinations are summarized in Table 1 and are depicted graphically in FIG. 1. In Table 1 the values given at times 0.5 through 6 hours are percentages of the corresponding values shown in Table 1 for Time 0. These results are depicted graphically in FIG. 1. Table 2 sets forth the percentages of hydrolysis to "free chlorine" experienced by the BCDMH and the DBDMH based on the results shown in Table 1. FIG. 2 depicts the results given in Table 2. It can be seen from Table 2 and FIG. 2 that over a time span of 6 hours the differences in the percentage of hydrolysis as between BCDMH and DBDMH remained substantially constant. The minor variations in such differences appearing in Table 2 and FIG. 2 are deemed insignificant statistically inasmuch as they are within experimental error.

TABLE 1

| Time, hr | BCDMH Free $Cl_2$ | BCDMH Total $Cl_2$ | DBDMH Free $Cl_2$ | DBDMH Total $Cl_2$ |
| --- | --- | --- | --- | --- |
| 0 | 23.1 | 100 | 98.8 | 100 |
| 0.5 | 25.6 | 104 | 100 | 104 |
| 1 | 23.1 | 100 | 85.1 | 87.3 |
| 1.5 | 17.9 | 92.3 | 87.3 | 87.3 |
| 2 | 16.6 | 88.5 | 81.6 | 83.9 |
| 3 | 16.6 | 88.5 | 70.1 | 74.7 |
| 4 | 30.7 | 79.5 | 65.5 | 66.6 |
| 5 | 15.4 | 76.9 | 60.1 | 63.2 |
| 6 | 10.2 | 71 | 59.8 | 62 |

TABLE 2

| Time, hr | BCDMH % hydrolysis to Free $Cl_2$ | DBDMH % hydrolysis to Free $Cl_2$ |
| --- | --- | --- |
| 0 | 23.1 | 98.8 |
| 0.5 | 24.7 | 95.6 |
| 1 | 23.1 | 97.3 |
| 1.5 | 19.4 | 100 |
| 2 | 18.8 | 97.2 |
| 3 | 18.8 | 93.8 |
| 4 | 38.7 | 93.8 |
| 5 | 20 | 96.4 |
| 6 | 14.3 | 96.3 |

EXAMPLE 2

The effectiveness of DBDMH and of BCDMH in microbiological control in cooling tower water was investigated in comparative tests. The cooling tower consisted of two 500-ton units in a crossflow design. The total system-contained volume was 14,000 gallons, and the tower contained medium efficiency film fill. Water from the tower cooled the coils of two 300-ton air conditioners (chillers). The tower typically operated at a pH of about 9.1 and 4 cycles of concentration. Blowdown was controlled by conductivity. Make-up water consisted of softened city water and which was of good quality. The make-up water was very low in calcium (<10 mg/L) but high in pH (8.7). The alkalinity was 145 mg/L (as $CaCO_3$), and the silica level was 28 mg/L. The tower employed a conventional polyphosphate/molybdate/phosphonate program to provide corrosion and deposit control. The conditions and results are summarized in Table 3.

TABLE 3*

|  | Cooling Tower Water | Make-up Water |
|---|---|---|
| Cooling Tower Data | | |
| Temperature (return line) | 91° F. | — |
| Temperature (to process) | 83° F. | — |
| Δ T | 8° F. | — |
| Make-up water | 4800 gal/day | — |
| Water Chemistry | | |
| Conductivity, mS/cm | 1.22 | 0.32 |
| pH, units | 9.2 | 8.7 |
| Alkalinity, mg/L as $CaCO_3$ | 480 | 145 |
| Total Hardness, mg/L as $CaCO_3$ | 1 | 3 |
| Silica, mg/L | 100 | 28 |

*This data represents the average of several analyses conducted during the course of the field trial.

The BCDMH (20 lbs) was introduced to the water using 20-gram, 1-inch tablets charged to a solid halogen feeder (Neptune model BT-40, Neptune Chemical Pump Co., Inc., Lansdale, Pa.). Before each dose, the cooling tower water was sampled and enumerated for heterotrophic bacteria plate counts. Then the tower was slug dosed three times a week with BCDMH. Slug dosing was accomplished by diverting through the feeder containing the tablets a sidestream of the recirculating water for about 1 to 5 hours until a "free chlorine" dose of about 0.5 mg/L (as "free chlorine") was obtained. The "total chlorine" dose was measured at the same time. After each dose the cooling water was sampled and enumerated for heterotrophic bacteria plate counts. As necessary, the feeder was replenished with more BCDMH tablets. The total dry weight of BCDMH tablets consumed over a 30-day test period (obtained by subtracting the dry weight of the tablets remaining in the feeder at the completion of the test from the total dry weight of the tablets added to the feeder during the test period) was found to be 25 lbs.

It was found that this biocide program (biocide dose 0.5 mg/L "free chlorine") reduced heterotrophic bacterial levels in the bulk water by an average of 1 order of magnitude. For example, before the biocide dose the bacteria levels in the bulk water ranged from $10^5$ to $10^4$ CFUs/mL. After the biocide dose the bacteria levels in the bulk water were reduced to $10^4$ to $10^3$.

After emptying the feeder of BCDMH tablets, 20 lbs of DBDMH granules was charged into the feeder. Thereupon the same procedure as described above for the BCDMH was carried out except for the fact that is was unnecessary to add any additional DBDMH to the feeder during the 30-day test period. In fact, the total weight of DBDMH consumed during the test was only 7 lbs. Also, the targeted 0.5 mg/L "free chlorine" dose in the bulk water was achieved in only 20 to 30 minutes. It was found that the biocidal performance provided by 7 lbs of DBDMH was the same as provided by 25 lbs of BCDMH under the same test conditions.

EXAMPLE 3

Using the same cooling tower as used in Example 2, the effectiveness of 1,3-dibromo-5,5-dimethylhydantoin in microbiological control in cooling tower water was investigated. As noted above, the cooling tower consisted of two 500-ton units in a crossflow design. The total system-contained volume was 14,000 gallons, and the tower contained medium efficiency film fill. Water from the tower cooled the coils of two 300-ton air conditioners (chillers). The tower typically operated at a pH of about 9.1 and 4 cycles of concentration. Blowdown was controlled by conductivity. Make-up water consisted of softened city water and which was of good quality. The make-up water was very low in calcium (<10 mg/L) but high in pH (8.7). The alkalinity was 145 mg/L (as $CaCO_3$), and the silica level was 28 mg/L. The tower employed a conventional polyphosphate/molybdate/phosphonate program to provide corrosion and deposit control.

The 1,3-dibromo-5,5-dimethylhydantoin was introduced to the water using granules charged to a solid halogen feeder (Neptune model BT-40, Neptune Chemical Pump Co., Inc., Lansdale, Pa.). The field trial lasted 51 days. The tower was slug dosed three times a week with 1,3-dibromo-5,5-dimethylhydantoin. Slug dosing was accomplished by diverting a sidestream of the recirculating water through the feeder containing the granules for about 1 to 5 hours until a total halogen residual of about 0.75 mg/L (as $Cl_2$) was obtained. This biocide program reduced bacterial levels in the bulk water by an average of 2 orders of magnitude, with bacteria levels in the bulk water after the biocide dose ranging from $10^1$ to $10^3$ CFUs/mL.

The results from the average of several analyses conducted during the course of this field trial using DBDMH were as follows: In the microbiological tests, the levels of aerobic bacteria were in the range of $6 \times 10^0$ to $3 \times 10^3$ CFUs/mL in the cooling tower water and $10^0$ in the make-up water. As regards water chemistry, the free halogen residual (as $Cl_2$) was 0.79 mg/L (the range being 1.9–0.00 mg/L) in the cooling tower water and 0.05 mg/L in the make-up water; and the total halogen residual (as $Cl_2$) was 0.82 mg/L (the range being 1.9–0.03 mg/L) in the cooling tower water and 0.8 mg/L in the make-up water.

The DBDMH utilized in the practice of this invention can be in the form of a powder, granules, caplets, tablets, briquettes, or pucks. A preferred process for producing highly suitable powder or particulate DBDMH and novel DBDMH products are described respectively in commonly-owned copending application Ser. Nos. 09/484,844 and 09/484,687, both filed Jan. 18, 2000. Methods for the formation of compacted forms of DBDMH such as caplets, tablets, briquettes and pucks are described in commonly-owned copending application Ser. No. 09/487,816, filed Jan. 18, 2000. Methods for producing DBDMH in granular form are described in commonly-owned copending application Ser. No. 09/483,896, filed Jan. 18, 2000. The disclosures of each of the foregoing applications are incorporated herein by reference as if fully set forth herein.

The methods of this invention thus involve use of 1,3-dibromo-5,5-dimethylhydantoin in compacted or in non-compacted forms. When used in compacted forms, the compacted forms can be produced without use of a binder provided that the average particle size of the 1,3-dibromo-5,5-dimethylhydantoin is at least 175 microns. Alternatively and more preferably, the compacted forms can be produced with use of a binder. A preferred type of binder for producing such compacted products is a saturated, normally solid, fatty amide as described in U.S. Pat. No. 5,565,576, issued Oct. 15, 1996 to L. K. Hall, J. A. Falter, and T. E. Farina, the disclosure of which patent is incorporated herein in toto as if fully set forth herein. In the practice of this invention such fatty amide binder is used with 1,3-dibromo-5,5-dimethylhydantoin having an average particle size of at least 175 microns. A particularly preferred type of binder for use in producing the compacted forms of 1,3-dibromo-5,5-dimethylhydantoin for use in this invention is a micronized synthetic polyolefin-based hydrocarbon wax and/or a micronized synthetic polyfluorocarbon wax effective to form the compacted product, provided the wax is suitably compatible with the 1,3-dibromo-5,5-dimethylhydantoin. In the practice of this invention with compacted forms of blends of 1,3-dibromo-5,5-dimethylhydantoin with a micronized synthetic polyolefin-based hydrocarbon wax and/or a micronized synthetic polyfluorocarbon wax, the average particle size of the 1,3-dibromo-5,5-dimethylhydantoin can be in the range of about 20 to about 600 microns, but preferably the average particle size of the 1,3-dibromo-5,5-dimethylhydantoin is in the range of about 175 to about 400 microns, if not even greater.

The amount of 1,3-dibromo-5,5-dimethylhydantoin used in practicing the methods of this invention is a biocidally effective amount, e.g., an amount which is at least sufficient to achieve substantial microbiological control, if not complete microbiological control, in the water being treated and/or substantial biofilm eradication, if not complete biofilm eradication, from the surfaces in contact with the water system being treated. Typically, dosages of 1,3-dibromo-5,5-dimethylhydantoin used for this purpose will fall within the range of about 0.1 to about 4.5 milligrams of "free chlorine" per liter of water (which corresponds to about 0.2 to about 10 milligrams of bromine, as $Br_2$, per liter of water). Preferably, such dosages are in the range of about 0.1 to about 2 milligrams of "free chlorine" per liter of water (which corresponds to about 0.2 to about 5 milligrams of bromine, as $Br_2$, per liter of water). However, departures from these ranges are permissible and are within the scope of this invention, provided that the departures result in sufficient microbiological control in accordance with the needs of the occasion, including applicable governmental regulations.

As noted above, the most effective presently-known process for producing 1,3-dibromo-5,5-dimethylhydantoin for use in the practice of this invention is described in commonly-owned copending application Ser. No. 09/484, 844, filed Jan. 18, 2000. That process comprises, for example, concurrently feeding (i) an aqueous solution or slurry formed from an inorganic base and 5,5-dimethylhydantoin, and (ii) abrominating agent in proportions such that each nitrogen atom is substituted by a bromine atom, thereby continuously forming product which precipitates in an aqueous reaction mixture. The pH of the mixture is continuously maintained in the range of about 5.5 to about 8.5. Examples 4–14 below illustrate that process. In Examples 4–14, pH was monitored by use of a pH meter. In Examples 4–13, bromine was fed using a Cole-Parmer Masterflex computerized drive and Easy-Load® pump head. When conducting the continuous operations of Examples 12 and 13, the resulting reaction slurry was collected manually and intermittently from the bottom of the reactor. Each fraction was collected in a 500 mL flask. These Examples do not constitute part of this invention. Instead they are presented to show best ways of making DBDMH.

EXAMPLE 4

235 Grams of NaOH (5.85 mol) are dissolved in 1800 g of water, and 375 g of 5,5-dimethylhydantoin (2.93 mol) is added to the NaOH solution. There are 935 g of $Br_2$ (5.85 mol) in the bromine reservoir. A 1-liter jacketed flask into which the $Br_2$ and the 5,5-dimethylhydantoin/NaOH solution are fed is maintained at 25° C. with a cooling bath. The 5,5-dimethylhydantoin/NaOH solution is co-fed to the reaction flask simultaneously with, but separately from, $Br_2$. The feed of the 5,5-dimethylhydantoin/NaOH solution was initiated shortly before (e.g., 3–4 min.) the initiation of the $Br_2$ feed. The feed rate of the 5,5-dimethylhydantoin/NaOH solution is 10 mL/minute, and the feed rate of the $Br_2$ is 1.60–1.70 mL/minute. The reaction mixture is stirred with a mechanical stirrer at a rate of 350–400 rpm. During the reaction, the pH ranged from 7.4 to 7.9. The slurry that forms as the reaction progresses is collected at a rate such that the level of the solution in the reaction flask remains constant. 500 mL fractions of product are collected through the bottom of the reaction flask, in an average time of 30 minutes per fraction. When the 5,5-dimethylhydantoin/ NaOH solution feed is finished, 86 g of $Br_2$ (0.54 mol) remains in the bromine reservoir.

Each product fraction is filtered and washed with three 500 mL portions of water, and the solid is then dried under a stream of nitrogen. The isolated yield of 1,3-dibromo-5, 5-dimethylhydantoin is 673 g, a yield of 80% based on 5,5-dimethylhydantoin, or a yield of 89% based on $Br_2$. The active bromine content is at least 99%, as determined by iodometric titration.

EXAMPLE 5

44 Grams of NaOH (1.1 mol) are dissolved in 338 g of water, and 70.4 g of 5,5-dimethylhydantoin (0.55 mol) is added to the NaOH solution. There are 175.1 g of $Br_2$ (1.1 mol) in the bromine reservoir. The reaction flask into which the $Br_2$ and the 5,5-dimethylhydantoin/NaOH solution are fed is maintained at 35° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.9 to 8.0. The reaction temperature stabilized at 37° C. during the 0.5 hour addition time. When the addition of reagents is finished, the orange slurry is filtered at 35° C. and washed with 650 mL of water. The resultant white solid is dried overnight under a stream of nitrogen. The isolated yield of 1,3-dibromo-5,5-dimethylhydantoin is 147.6 g, a yield of 94%, and the active bromine content of the 1,3-dibromo-5, 5-dimethylhydantoin is 55.1 wt % (98.6% of the theoretical value), as determined by iodometric titration. cl EXAMPLE 6

44 Grams of NaOH (1.1 mol) are dissolved in 338 g of water, and 70.4 g of 5,5-dimethylhydantoin (0.55 mol) is added to the NaOH solution. There are 172.0 g of $Br_2$ (1.07 mol) in the bromine reservoir. The reaction flask into which the $Br_2$ and the 5,5-dimethylhydantoin/NaOH solution are fed is maintained at 67° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The bromine is diluted with nitrogen and fed below the surface of the solution in the reaction flask. The reaction mixture is stirred with a mechanical stirrer at a rate of 400 rpm; the pH ranged from 6.7 to 7.1 during the reaction. During the 0.5 hour addition time, the reaction temperature stabilized at 67° C. When the addition of reagents is finished, the orange slurry is discharged from the reaction flask into a beaker and allowed to cool slowly. The slurry is filtered at ~45° C. and washed with two 500 mL portions of water. The resultant white solid is dried overnight under a stream of nitrogen. The isolated yield of 1,3-dibromo-5,5-dimethylhydantoin is 130.5 g, a yield of ~83% based on 5,5-dimethylhydantoin, or a yield of ~85% based on $Br_2$. The active bromine content of the 1,3-dibromo-5,5-dimethylhydantoin is 55.9 wt % (100% of the theoretical value), as determined by iodometric titration. Particle size data on the 1,3-dibromo-5,5- dimethylhydantoin product formed in this operation based on a representative dried sample of the product are summarized in Table 4.

TABLE 4

| Particle Size Category | Particle Size of Product |
|---|---|
| Average | 237.5μ |
| 10% is greater than | 371.6μ |
| 25% is greater than | 309.8μ |
| 50% is greater than | 239.1μ |
| 75% is greater than | 165.6μ |
| 90% is greater than | 99.81μ |
| Range | 0.040–541.9μ |

EXAMPLE 7

354 Grams of NaOH (8.85 mol) are dissolved in 2700 g of water. 562 g of 5,5-dimethylhydantoin (4.386 mol) is added to the NaOH solution. The reaction flask is charged with 500 mL heel of a 1,3-dibromo-5,5-dimethylhydantoin filtrate (mother liquor). The 5,5-dimethylhydantoin/NaOH solution is co-fed to the jacketed reaction flask, no heating or cooling is applied simultaneously with, but separately from, $Br_2$. The feed rate of the 5,5-dimethylhydantoin/NaOH solution is 10 mL/minute, and the feed rate of the $Br_2$ is initially 1.70 mL/minute, but is adjusted later to 1.68 mL/minute to maintain the pH of the reaction mixture at ~7.0. The reaction mixture is stirred with a mechanical stirrer at a rate of 400 rpm reaction temperature is stabilized at about 42° C. The slurry that forms as the reaction progresses is collected at a rate such that the level of the solution in the reaction flask remains constant. Eight 500 mL fractions of product were collected through the bottom of the reaction flask, in an average time of 30 minutes per fraction. A total of 1374.5 g of $Br_2$ (8.59 mol) are added during the reaction.

Each product fraction is filtered and washed with a 500 mL portion of water; the solids are then dried overnight at 50° C. in a vacuum oven. The total isolated yield of 1,3-dibromo-5,5-dimethylhydantoin is 1152 g, a yield of 92% based on 5,5-dimethylhydantoin, or a yield of 94% based on $Br_2$. The active bromine content of the 1,3-dibromo-5,5-dimethylhydantoin ranges from 55.4 wt % to 55.7 wt % (99.1% to 99.7% of the theoretical value), as determined by iodometric titration. The average particle size of the 1,3-dibromo-5,5-dimethylhydantoin is greater than 150μ.

EXAMPLE 8

89 Grams of NaOH (2.2 mol) are dissolved in 676 g of water, and 141 g of 5,5-dimethylhydantoin (1.1 mol) is added to the NaOH solution. There are 350 g of $Br_2$ (2.2 mol) in the bromine reservoir. The reaction flask into which the $Br_2$ and the 5,5-dimethylhydantoin/NaOH solution are fed is maintained at 67° C. with a heating bath. The reaction flask is charged with ~400 mL heel (483 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.1. The reaction temperature stabilized at 67° C. during the 66 minute addition time. When the addition of reagents is finished, the orange slurry is filtered at 43° C. and washed with 1000 mL (2×500 mL) of water. The resultant white solid is dried overnight under a stream of nitrogen. 307.3 Grams of $Br_2$ (1.92 mol) had been fed to the reaction flask. The isolated yield of 1,3-dibromo-5,5-dimethylhydantoin is 212.5 g, a yield of 77% based on $Br_2$, and 68% based on 5,5-dimethylhydantoin; the active bromine content of the 1,3-dibromo-5,5-dimethylhydantoin is 55.9 wt % (100% of the theoretical value), as determined by iodometric titration.

EXAMPLE 9

88 Grams of NaOH (2.2 mol) are dissolved in 338 g of water, and 140.8 g of 5,5-dimethylhydantoin (1.1 mol) is added to the NaOH solution. There are 352 g of $Br_2$ (2.2 mol) in the bromine reservoir. The reaction flask into which the $Br_2$ and the 5,5-dimethylhydantoin/NaOH solution are fed is maintained at 69° C. with a heating bath. The reaction flask is charged with ~200 mL heel (240 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.0. The reaction temperature stabilized at 68–69° C. during the 39 minute addition time. When the addition of reagents is finished, the orange slurry is filtered at 40° C. and washed with 500 mL of water. The resultant white solid is dried overnight under a stream of nitrogen. 285.5 Grams of $Br_2$ (1.78 mol) had been fed to the reaction flask. The isolated yield of 1,3-dibromo-5,5-dimethylhydantoin is 186.8 g, a yield of 73% based on $Br_2$, and 60% based on 5,5-dimethylhydantoin; the active bromine content of the 1,3-dibromo-5,5-dimethylhydantoin is 53.4 wt % (96% of the theoretical value), as determined by iodometric titration.

Table 5 summarizes the particle size data for the products of Examples 8 and 9.

TABLE 5

| Particle Size Category | Particle Size of Product - Example 8 | Particle Size of Product - Example 9 |
|---|---|---|
| Average | 210.4μ | 293.6μ |
| 10% is greater than | 381.7μ | 451.2μ |
| 25% is greater than | 298.3μ | 349.6μ |
| 50% is greater than | 196.8μ | 256.3μ |
| 75% is greater than | 115.3μ | 174.9μ |
| 90% is greater than | 56.86μ | 110.6μ |
| Range | 0.040–594.9μ | 0.040–>2000μ |

EXAMPLE 10

44.2 Grams of NaOH (1.1 mol) are dissolved in 338 g of water, and 70.4 g of 5,5-dimethylhydantoin (0.55 mol) is added to the NaOH solution. There are 173 g of $Br_2$ (1.08 mol) in the bromine reservoir. The reaction flask into which the $Br_2$ and the 5,5-dimethylhydantoin/NaOH solution are fed is maintained at 57° C. with a heating bath. The reaction flask is charged with ~200 mL heel (244 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 57° C. during the 33 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 139.8 g, a yield of 91% based on $Br_2$, and 89% based on 5,5-dimethylhydantoin; the active bromine content of the 1,3-dibromo-5,5-dimethylhydantoin is 55.7 wt % (99.7% of the theoretical value), as determined by iodometric titration.

EXAMPLE 11

44.2 Grams of NaOH (1.1 mol) are dissolved in 338 g of water, and 70.3 g of 5,5-dimethylhydantoin (0.55 mol) is added to the NaOH solution. There are 172.5 g of $Br_2$ (1.08 mol) in the bromine reservoir. The reaction flask into which the $Br_2$ and the 5,5-dimethylhydantoin/NaOH solution are fed is maintained at 48° C. with a heating bath. The reaction flask is charged with ~200 mL heel of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 48° C. during the 34 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 144.8 g, a yield of 94% based on $Br_2$, and 92% based on 5,5-dimethylhydantoin; the active bromine content of the 1,3-dibromo-5,5-dimethylhydantoin is 55.0 wt % (98.4% of the theoretical value), as determined by iodometric titration.

The particle size data for the products of Examples 10 and 11 are summarized in Table 6.

TABLE 6

| Particle Size Category | Particle Size of Product - Example 10 | Particle Size of Product - Example 11 |
| --- | --- | --- |
| Average | 231.2μ | 178.4μ |
| 10% is greater than | 338.3μ | 281.1μ |
| 25% is greater than | 285.0μ | 230.9μ |
| 50% is greater than | 228.8μ | 175.7μ |
| 75% is greater than | 177.8μ | 125.0μ |
| 90% is greater than | 133.0μ | 79.14μ |
| Range | 0.040–493.6μ | 0.040–409.6μ |

EXAMPLE 12

The process of this Example was conducted in a continuous fashion. A feed solution of 5,5-dimethylhydantoin/NaOH was formed by adding 5,5-dimethylhydantoin to a 9 wt % NaOH solution, such that the 5,5-dimethylhydantoin concentration was about 1.1 M. The 5,5-dimethylhydantoin/NaOH solution was co-fed to the reaction flask simultaneously with, but separately from, $Br_2$. The flask was suspended in a heating bath. The reaction mixture was stirred with a mechanical stirrer at a rate of 500 rpm. The reaction mixture was maintained at a pH of about 7.0±0.2, and the reaction temperature was maintained at 55° C. Ten fractions of product were collected in an average time of 30 minutes per fraction. The isolated yield of the 1,3-dibromo-5,5-dimethylhydantoin was 90% based on 5,5-dimethylhydantoin, and 92% based on added $Br_2$. The purity of the 1,3-dibromo-5,5-dimethylhydantoin, a white crystalline product, was 99.8%, based on the theoretical bromine content. Fractions 5–10 represent the particle size of the product as formed during steady-state operating conditions. Table 7 summarizes average particle size data and particle size distribution data relating to fractions 5–10 based on samples of each such fraction taken during the steady-state operation of the continuous process. The determinations showed that a bimodal distribution of the product had been produced. The overall average particle size of the product was 512.3 microns.

TABLE 7

| Particle Size | Fraction 5 | Fraction 6 | Fraction 7 | Fraction 8 | Fractions 9 + 10 |
| --- | --- | --- | --- | --- | --- |
| Average | 371.7μ | 445.6μ | 535.5μ | 560.3μ | 545.9μ |
| 10% is greater than | 530.7μ | 626.0μ | 724.7μ | 805.0μ | 952.1μ |
| 25% is greater than | 462.2μ | 550.9μ | 643.3μ | 729.3μ | 833.4μ |
| 50% is greater than | 386.0μ | 474.5μ | 559.7μ | 641.8μ | 676.7μ |
| 75% is greater than | 256.8μ | 369.6μ | 447.8μ | 436.1μ | 149.6μ |
| 90% is greater than | 94.76μ | 134.4μ | 150.3μ | 94.5μ | 76.02μ |
| Range | 0.791–786.9μ; 1255–1512μ | 4.241–786.9μ; 1143–1255μ | 3.519–863.9μ; 1143–1512μ | 3.519–8.639μ; 1143–1512μ | 0.721–409.6μ; 493.6–1255μ |

EXAMPLE 13

Another continuous operation was conducted in a manner similar to that of Example 12. The feed solution was formed by dissolving 355 g (8.87 mols) in 3550 g of water. To this was added 560 g (4.37 mols) of 5,5-dimethylhydantoin. The concurrent feeds were adjusted to maintain the pH of the aqueous reaction mixture at 7.0±0.2. The temperature was maintained at 55° C. The total amount of bromine ($Br_2$) fed was 1359.4 g (8.50 mols). As in Example 12, ten fractions of the reaction mixture were collected. However, in this operation, the addition rates were adjusted such that the average residence time was approximately 1 hour per fraction. The total isolated yield of 1,3-dibromo-5,5-dimethylhydantoin was 88% based on 5,5-dimethylhydantoin used and 90% based on the added bromine. The 1,3-dibromo-5,5-dimethylhydantoin product was obtained as a white crystalline solid. Table 8 summarizes the average particle size data and product distribution data relating to the product formed in this reaction. Fractions 5–10 represent the particle size of the product as formed during steady-state operating conditions. As in Example 12, the product formed was bimodal. In Table 8 "n.d." indicates that the particle size determination for the larger particle sized fraction was not determined; the instrument used could not measure particles having a particle size greater than 2000 microns. The overall average particle size of the product was at least 455.5 microns.

was 4.67 grams/minute via a Masterflex Easy-Load peristaltic pump. The reaction mixture was stirred at 400 rpm. The pH of the reaction was monitored by measuring the pH of the effluent using a pH meter, and the pH ranged from 6.06 to 6.36 during the reaction. Product removal from the reactor was also controlled by a pump. Residence time was, on average, 30 minutes per fraction; each fraction was about 500 mL. A yield of 90.5% of 1,3-dibromo-5,5-dimethylhydantoin was obtained, based on the amount of 5,5-dimethylhydantoin fed to the reactor. The active bromine content of the 1,3-dibromo-5,5-dimethylhydantoin was >55.3%, as determined by standard iodometric titration. Thus, the purity of this product was greater than 99.0%.

Table 9 summarizes particle size data on the 1,3-dibromo-5,5-dimethylhydantoin product formed in the continuous operation of Example 14. These data are averaged data based on two samples taken at different times during the continuous operation once steady state conditions, or essentially steady state conditions, had been achieved.

TABLE 9

| Particle Size Category | Particle Size of Product |
| --- | --- |
| Average | 188.9μ |
| 10% is greater than | 295.2μ |
| 25% is greater than | 255.6μ |
| 50% is greater than | 203.1μ |
| 75% is greater than | 122.5μ |
| 90% is greater than | 55.9μ |
| Range | 0.872–356.5μ |

TABLE 8

| Particle Size | Fraction 5 | Fraction 6 | Fraction 7 | Fraction 8 | Fractions 9 + 10 |
| --- | --- | --- | --- | --- | --- |
| Average | 421.2μ | 478.6μ | 494.0μ | 536.6μ | 631.9μ |
| 10% is greater than | 606.5μ | 699.1μ | 781.7μ | 1063μ | 1438μ |
| 25% is greater than | 532.1μ | 623.4μ | 681.5μ | 813.9μ | 995.7μ |
| 50% is greater than | 452.3μ | 535.0μ | 548.5μ | 546.7μ | 522.8 |
| 75% is greater than | 340.0μ | 372.2μ | 176.6μ | 150.3μ | 160.7μ |
| 90% is greater than | 140.8μ | 112.8μ | 68.94μ | 72.93 | 81.68μ |
| Range | 2.423–786.9μ; n.d. | 2.423–863.9μ; n.d. | 1.520–863.9μ; 1255–1512μ | 0.04–2000μ; n.d. | 0.04–>2000μ; n.d. |

EXAMPLE 14

Another continuous operation was performed using a glass reactor into which were concurrently fed, on a continuous basis, an aqueous solution of 5,5-dimethylhydantoin and NaOH, and a separate feed of bromine. The aqueous solution was made by adding 5,5-dimethylhydantoin to an aqueous 9 wt % NaOH solution. This solution contained about 22.4 wt % of 5,5-dimethylhydantoin and 7 wt % NaOH. A one liter, jacketed reactor having an interior diameter of 82 millimeters equipped with an anchor agitator, with an outer diameter of 72 millimeters, was used, and a silicone fluid (Rhodersil 4720V20 fluid; Rhone-Poulenc) was circulated through the jacketing. The temperature of the reaction was controlled at 38° C. Both feeds were controlled by pumps; the average feed rate of the 5,5-dimethylhydantoin/NaOH solution was 15.84 grams/minute via a Prominent Gamma G/4A positive displacement pump, and the average feed rate of the bromine Examples 15 and 16 illustrate methods of producing tablets from large average particle size 1,3-dibromo-5,5-dimethylhydantoin without use of binders, and the exceptional crush strength of such binder-free tablets. Example 17 illustrates the excellent flowability characteristics and low-dusting properties possessed by the large average particle size 1,3-dibromo-5,5-dimethylhydantoin.

EXAMPLE 15

Five gram samples of 1,3-dibromo-5,5-dimethylhydantoin produced by the process referred to above were compacted without binder in a Sintech® press (MTS Systems Corporation, Edenprairie, Minn.) equipped with a punch and die fabricated from Hastelloy® C alloy. Prior to filling the die, the interior surfaces of the die were lightly dusted with a micronized polypropylene wax (MICROPRO 400 wax; Micro Powders, Incorporated, Tarrytown, N.Y.) to serve as a lubricant. The pressure applied was 5000 psi with no dwell time, i.e., the pressure was automatically terminated immediately upon reaching 5000 psi. The resultant tablets after removal from the die were aged for 6 days at room temperature. Thereupon the tablets were subjected to crush strength testing utilizing a Sintech® 1/S compression apparatus (MTS Systems Corporation, Edenprairie, Minn.) equipped with Testworks software, which software is installed in the 1/S compression apparatus as supplied by MTS Systems Corporation. The apparatus includes a horizontal circular-shaped load cell interfaced with a computer, a digital micrometer also interfaced with the computer, and a vertical screw-driven piston that is disposed above the load cell and adapted to apply a downward force perpendicular to the load cell. The procedure for measuring crush strength involves measuring the thickness of the tablet with the micrometer to provide a digitized input to the computer. Next the tablet is placed on its edge on the load cell with the piston in contact with the upper edge of the tablet. Then the apparatus is activated whereby the piston commences applying a progressively increasing downward diametral force to the tablet. At the same time, the load cell continuously measures the downward force being applied to the tablet, and the input of such measurements is transmitted to the computer. When the force being applied reaches the point where the amount of force suddenly decreases to 10% of the immediately preceding force, the tablet has reached the breaking point, and the application of the force is immediately terminated by the software program. From the inputs to the computer, two values are provided, namely the pounds of force at the breaking point of the tablet, and the pounds of force per inch thickness of the tablet at the breaking point. Thus the greater the force applied, the greater the strength. Two groups of such tests were conducted. One set (Set A) involved forming and evaluating 5 tablets from a batch of 1,3-dibromo-5,5-dimethylhydantoin produced in a continuous process described in Example 13. The other set (Set B) of tests involved 3 tablets produced from another batch of 1,3-dibromo-5,5-dimethylhydantoin produced in a batch process of the type described in Example 9. Table 10 summarizes the results of these tests.

TABLE 10

| Test Set | Tablet Thickness | Crush Strength | Crush Strength |
|---|---|---|---|
| A | 0.365 in. | 20.9 lb. | 57.3 lb./in. |
| A | 0.367 in. | 25.5 lb. | 69.5 lb./in. |
| A | 0.366 in. | 19.2 lb. | 52.5 lb./in. |
| A | 0.367 in. | 22.8 lb. | 62.1 lb./in. |
| A | 0.364 in. | 23.7 lb. | 65.0 lb./in. |
| Avg. of A | — | 22.4 lb. | 61.3 lb./in. |
| B | 0.353 in. | 10.7 lb. | 30.4 lb./in. |
| B | 0.352 in. | 12.8 lb. | 36.4 lb./in. |
| B | 0.354 in. | 9.8 lb. | 27.8 lb./in. |
| Avg. of B | — | 11.1 lb. | 31.5 lb./in. |

Tablets of conventional, small particle sized 1,3-dibromo-5,5-dimethylhydantoin devoid of binder cannot be tableted in the manner described above.

EXAMPLE 16

The crush strength of tablets formed from 1,3-dibromo-5,5-dimethylhydantoin formulated with a binder was illustrated in a group of tests conducted as described in Example 15. The procedure for producing the tablets was as follows: 1,3-dibromo-5,5-dimethylhydantoin produced as in Example 14 was hand-mixed with 3% by weight of micronized polyethylene wax from Micro Powders Incorporated, Tarrytown, N.Y. for approximately 30 minutes. The resultant formulation was then converted into tablets as described in Example 15. The results of the crush strength tests, conducted as described in Example 15, are summarized in Table 11.

TABLE 11

| Tablet Thickness | Crush Strength | Crush Strength |
|---|---|---|
| 0.372 in. | 39.8 lb. | 107.2 lb./in. |
| 0.375 in. | 44.9 lb. | 119.9 lb./in. |
| 0.375 in. | 37.5 lb. | 100.0 lb./in. |
| 0.375 in. | 36.1 lb. | 96.5 lb./in. |
| 0.377 in. | 37.6 lb. | 99.7 lb./in. |
| Averaged Results | 39.2 lb. | 104.6 lb./in. |

EXAMPLE 17

Comparative flowability tests were carried out using a sample of 1,3-dibromo-5,5-dimethylhydantoin and samples of commercially-available 1,3-dihalo-5,5-dimethylhydantoin products. These tests involved filling an 8-ounce glass jar to about one-third of its capacity with the sample to be tested. After closing the jar, it was slowly rotated while on its side in a single direction while observing the characteristics of the contents. Table 12 summarizes the observations made in these flowability tests. In Table 14 the following abbreviations are used:

DBDMH is 1,3-dibromo-5,5-dimethylhydantoin
DCDMH is 1,3-dichloro-5,5-dimethylhydantoin
BCDMH is N,N'-bromochloro-5,5-dimethylhydantoin

TABLE 12

| N,N'-dihalohydantoin | Average Particle Size | Source | Product Characteristics |
|---|---|---|---|
| DCDMH | 108.1 microns | Aldrich Chemical Co. | Bridging occurred; high dusting, non-free-flowing powder |
| BCDMH | 323.8 microns | Aldrich Chemical Co. | Bridging occurred; high dusting, non-free-flowing powder |
| DBDMH | 162.1 microns | Aldrich Chemical Co. | Bridging occurred; high dusting, non-free-flowing powder |
| DBDMH | 64.5 microns | Albemarle Corporation | Bridging occurred; high dusting, non-free-flowing powder |
| DBDMH | 45.2 microns | Great Lakes Chemical Corporation | Bridging occurred; high dusting, non-free-flowing powder |
| DBDMH | 293.6 microns | The new process of application Ser. No. 09/484,844 | No bridging occurred; low dusting, free-flowing powder |

Examples 18–26 illustrate the preparation and properties of compacted products formed from 1,3-dibromo-5,5-dimethylhydantoin utilizing novel binders as described in commonly-owned copending application Ser. No. 09/487,816, filed Jan. 18, 2000.

EXAMPLE 18

2.5 Grams of a micronized polyethylene wax (MPP-611, Micro Powders Inc., Tarrytown, N.Y.), was weighed into a crystallizing dish, followed by 1,3-dibromo-5,5-dimethylhydantoin (47.5 g). A broad-bladed spatula was used to blend the mixture rather like a cook might blend butter into flour. After 10 minutes of hand mixing in this fashion, the product was admitted to a glass bottle which was rolled to assess the flowability of the mixture. The flow properties were improved over the properties of the 1,3-dibromo-5,5-dimethylhydantoin used to make the blend.

EXAMPLE 19

2.5 Grams of polypropylene wax (MICROPRO 400, Micro Powders Inc., Tarrytown, N.Y.), was weighed into a crystallizing dish, followed by 1,3-dibromo-5,5-dimethylhydantoin (47.5 g). This mixture was blended as described in Example 18, and transferred to a glass bottle which was rolled to assess the flowability of the blend. Its flow properties were improved over the properties of the 1,3-dibromo-5,5-dimethylhydantoin used to make the blend.

EXAMPLE 20

The 1,3-dibromo-5,5-dimethylhydantoin blends prepared in Examples 18 and 19 were subjected to a compaction test. Each sample was weighed, and introduced into a 0.71 inch diameter die made from Hastelloy® C alloy and compacted with a screw-driven punch, also made of Hastelloy® C alloy, to a pre-set pressure. Before filling the die, its interior surfaces were lightly dusted with micronized polypropylene wax to serve as a lubricant. There was no dwell time upon attaining the compaction pressure (the pressure was released immediately). Upon extracting the tablet from the die, the thickness of the tablet was measured with a micrometer, and a visual observation of the tablet was made.

For comparison, the blends were compared to unblended, virgin, commercially produced 1,3-dibromo-5,5-dimethylhydantoin powder with an average particle size of about 64.5µ, and a commercial toilet bowl product (abbreviated in Table 13 as CTB product), which is known to be a mixture of other halogenated hydantoin compounds. This toilet bowl puck was purchased from a supermarket and ground to a powder with a mortar and pestle, and recompacted as above described.

Table 13 lists the experimental conditions and the observations.

TABLE 13

| Blend | Amount of blend added to die | Pressure | Tablet thickness | Observations |
|---|---|---|---|---|
| DBDMH/5 wt % MPP-611 | 5.0 g | 5000 psi | 0.389 in. | Intact tablet, smooth shiny surfaces |
| DBDMH/5 wt % Micropro 400 | 5.0 g | 5000 psi | 0.374 in. | Intact tablet, not 100% mold release from top punch |
| DBDMH | 2.5 g | 5000 psi | — | compact shattered and laminated on removal from die |
| CTB product | 2.5 g | 5000 psi | 0.22 in. | Intact tablet |

EXAMPLE 21

The 1,3-dibromo-5,5-dimethylhydantoin/5 wt % MPP-611 tablets produced in Example 19 were placed in glass beakers of water. The tablet appeared to do nothing. Its physical integrity remained intact as it slowly dissolved over a period of several months. In order to prove that it was releasing dissolved halogen, the tablet was removed from the water, washed with deionized water and dried with a paper towel. A plastic wash bottle was then used to wash the tablet into a deionized water solution containing N,N-diethyl-phenylenediamine (DPD) powder. This solution immediately turned pink when the wash pressure on the tablet until it breaks. The pressure required to reach the breaking point is recorded and reported as the crush strength.

The crush strength of the tablets was compared to a commercial toilet bowl product (abbreviated as CTB product in Table 15). This was purchased from a supermarket, ground to a powder and re-compacted under the conditions described above.

Table 15 summarizes the observations and results. The crush strength data represent an average of 3 separate measurements.

TABLE 15

| Blend | Average thickness | Average crush strength | Observations |
|---|---|---|---|
| DBDMH/5 wt % MPP-611 | 0.38 in. | 93.7 lb./in.* | Single tablets, shiny surfaces, low dust |
| DBDMH/3 wt % MPP-611 | 0.38 in. | 57.9 lb./in. | Single tablets, shiny surfaces, low dust |
| DBDMH/2 wt % MPP-611 | 0.37 in. | 37.0 lb./in. | Single tablets, shiny surface, low dust |
| CTB product | 0.44 in. | 55.2 lb./in. | Single tablets, dull surfaces, dusty |

*An estimate because 2 of the 3 tablets did not break before the limit of the load cell was exceeded.

The data in Table 15 clearly demonstrate that the crush strength of the tablets is a function of the micronized polyethylene wax loading, and that when using micronized polyethylene wax with 1,3-dibromo-5,5-dimethylhydantoin, it is possible to obtain a stronger product than a commercial toilet bowl product.

EXAMPLE 22

1,3-Dibromo-5,5-dimethylhydantoin was blended with micronized polyethylene wax (MPP-611) such that the blend contained 3 wt % of the wax. A sample of the blend (5 g) was introduced to a die made from Hastelloy® C alloy, and compacted to a pressure of 5000 psi. Three more samples (5 g each) were compacted in the same manner, and each time a single tablet was extracted from the die after the pressure had been released. In each case, before filling the die, its interior surfaces were lightly dusted with micronized polypropylene wax to serve as a lubricant. The tablets were manually broken into two equally-sized pieces. One half of each tablet was crushed into a powder with a mortar and pestle, and the powder was titrated to determine its wt % of active bromine. The other half of each tablet was placed in a sealed glass vial and placed in an oven at 50° C. After 30 days, the samples were removed from the oven, ground up, and titrated to determine its wt % of active bromine. For comparative purposes, a control sample of commercially produced 1,3-dibromo-5,5-dimethylhydantoin having an average particle size of about 64.5µ (containing no micronized polyethylene wax) was subjected to the same operations. In the case of this control sample, was not possible to extract a single tablet from the die, and thus only shattered laminates could be tested.

Table 14 lists the results obtained for four samples of 1,3-dibromo-5,5-dimethylhydantoin/3 wt % micronized polyethylene wax blends, along with the control sample containing no additive.

TABLE 14

| | Wt % Active Bromine | |
| --- | --- | --- |
| | Initial | After 30 days |
| Sample 1 | 53.4 | 53.3 |
| Sample 2 | 53.3 | 53.6 |
| Sample 3 | 54.2 | 53.3 |
| Sample 4 | 53.3 | 53.7 |
| Control | 55.3 | 55.2 |

The data in Table 14 indicate that, within the reproducibility of the analytical technique used, the presence of 3 wt % of micronized polyethylene wax in a 1,3-dibromo-5,5-dimethylhydantoin tablet does not induce a loss of active bromine after storage at 50° C. for 30 days. This absence of active bromine loss demonstrates the chemical compatibility of 1,3-dibromo-5,5-dimethylhydantoin and micronized polyethylene wax.

EXAMPLE 23

The strength of 1,3-dibromo-5,5-dimethylhydantoin tableted with different amounts of micronized polyethylene wax, as described in Example 22, was measured in a series of crush strength tests. In each test, 5 g of blended material was added to a die made from Hastelloy® C alloy and compressed with a screw-driven punch, also made from Hastelloy C alloy, to a pressure of 5000 psi. In each case, before filling the die, the interior surfaces of the die were lightly dusted with micronized polypropylene wax to serve as a lubricant. After extraction of the tablet from the die, a visual observation of the tablet was made.

A Sintech® 1/S compression apparatus equipped with Testworks software was used to determine the crush strength of the tablets. This uses a screw-driven piston to exert dibromo-5,5-dimethylhydantoin having an average particle size of about $64.5\mu$. Tableting and crush strength testing were performed as described in Examples 22 and 23.

The crush strength of the tablets was compared to a commercial toilet bowl product (abbreviated as CTB product in Table 16). This commercial toilet bowl product was purchased from a supermarket, ground to a powder, and re-tableted under the conditions described in Example 22.

Table 16 summarizes the observations and results. The crush strength data represent an average of 3 separate measurements.

TABLE 16

| DBDMH blend | Average thickness | Average crush strength | Observations |
| --- | --- | --- | --- |
| Polyfluo 200 wax | 0.38 in. | 30.2 lb/in. | Single tablets, tend to end-cap on breaking |
| Polyfluo 400 wax | 0.37 in. | 22.2 lb/in. | Single tablets, tend to end-cap on breaking |
| Micropro 400 wax | 0.36 in. | 11.8 lb/in. | Single tablets, tend to end-cap on breaking |
| Synfluo 180 VF | 0.38 in. | 37.8 lb/in. | Single tablets, tend to end-cap on breaking |
| Polysilk 600 | — | — | Powder is discolored, chemical incompatibility; no tablets were made |
| Handy Tack 140 resin | 0.39 in. | 27.5 lb/in. | Tablets are discolored, chemical incompatibility |
| CTB product | 0.44 in. | 102.3 lb/in. | Single tablets |

Although in the tests summarized in Table 16 the 1,3-dibromo-5,5-dimethylhydantoin tablets were not as strong as the prepared sample of CTB product, nevertheless all of the micronized waxes served as effective binders for 1,3-dibromo-5,5-dimethylhydantoin in that they produced whole tablets that remained intact when extracted from a die, and that exhibited adequate crush strength. However, a micronized modified petroleum resin (Handy Tack 140, Micro Powders Inc., Tarrytown, N.Y.) and a fluorinated hydrocarbon mixture (Polysilk 600, Micro Powders Inc., Tarrytown, N.Y.) both displayed signs of chemical incompatibility with 1,3-dibromo-5,5-dimethylhydantoin.

EXAMPLE 24

A series of different blends was prepared using a variety of micronized waxes (purchased from Micro Powders Incorporated, Tarrytown, N.Y.). Each blend was prepared in the fashion described in Example 18, such that the blend contained 3 wt % wax. The source of the DBDMH used in forming these blends was commercially produced 1,3-water was introduced, proving that soluble halogen was being washed from the tablet. In this connection, DPD is an indicator of high sensitivity used to detect the presence of soluble halogen at the parts per million level. In the presence of such quantities of dissolved halogen, the DPD turns pink.

EXAMPLE 25

Blending and tableting studies were scaled up. A ribbon blender with a volume of two cubic feet was used to mix 25 kg of commercially produced 1,3-dibromo-5,5-dimethylhydantoin, having an average particle size of about $64.5\mu$, with micronized polyethylene wax (MPP-611) to achieve loadings of 2.0 wt % and 2.5 wt % of wax. The mixing time was 60 minutes in each case. A double-cone, tumble blender with a volume of 5 cubic feet was used to tumble mix 25 kg of 1,3-dibromo-5,5-dimethylhydantoin with micronized polyethylene wax to achieve a loading of 3 wt % of wax. The mixing time was 240 minutes.

Each blend was passed through a Chilsonator® breaker (The Fitzpatrick Company, Elmhurst, Ill.) and a set of screens to produce compacted granules of U.S. mesh size 12 to 18. Virgin, commercially-produced 1,3-dibromo-5,5-dimethylhydantoin having an average particle size of about $64.5\mu$, without micronized polyethylene wax, was also passed through the same equipment. This material did not compact and form granules. Instead, material exiting the Chilsonator® was mostly loose powder.

The granules of each 1,3-dibromo-5,5-dimethylhydantoin/micronized polyethylene wax blend were introduced to the feed hopper of a rotary tablet press. The turret contained 18 die cavities, each of which is 0.75 inches in diameter, which was automatically filled with granules and compressed between two punches made of Hastelloy® C alloy. The tablets ejected from the tablet press were collected, and 7 days later were subject to crush strength testing. The results given in Table 17 are an average of at least 3 tests.

TABLE 17

| DBDMH Blend | Tablet Thickness | Crush strength |
|---|---|---|
| 2 wt % MPP-611, tumble blender | 0.49 in. | 16.6 lb/in |
| 2.5 wt % MPP-611, Ribbon blender | 0.49 in. | 19.3 lb/in |
| 3 wt % MPP-611, Ribbon blender | 0.72 in. | 24.1 lb/in |

The main findings from the runs of Example 25 were that the commercially produced 1,3-dibromo-5,5-dimethylhydantoin with an average particle size of about 64.5$\mu$ alone cannot be compacted into granules suitable for making tablets, and that the presence of micronized polyethylene wax (MPP-611) with such finely-divided 1,3-dibromo-5,5-dimethylhydantoin promotes the process of compaction into granules. These granules can be fed to a tableting machine and compacted into tablets. The strength of the tablets is governed by the amount of micronized polyethylene wax present. The higher the level of micronized polyethylene wax, the stronger the tablet.

EXAMPLE 26

The crush strength of tablets formed from a large average particle sized 1,3-dibromo-5,5-dimethylhydantoin formulated with a binder was measured. This 1,3-dibromo-5,5-dimethylhydantoin had an average particle size of about 189 microns, and the binder was a micronized polyethylene wax (MPP-611), and the binder was 3 wt % of the blend. The measurements were made utilizing a Sintech 1/S compression apparatus equipped with Testworks software. In these tests the tablets were subjected to increasing force applied along the longitudinal axis of the tablet until breakage occurred. The procedure for producing the tablets was as described in Example 21. The results of the crush strength tests are summarized in Table 18.

TABLE 18

| Tablet Thickness | Crush Strength | Crush Strength |
|---|---|---|
| 0.372 in. | 39.8 lb. | 107.2 lb./in. |
| 0.375 in. | 44.9 lb. | 119.9 lb./in. |
| 0.375 in. | 37.5 lb. | 100.0 lb./in. |
| 0.375 in. | 36.1 lb. | 96.5 lb./in. |
| 0.377 in. | 37.6 lb. | 99.7 lb./in. |
| Averaged Results | 39.2 lb. | 104.6 lb./in. |

As can be seen from the foregoing description, there are a great number of important ways of carrying out or implementing this invention. In brief summary, some of these embodiments are as follows:

A) a method of effecting microbiocidal activity in a body of water, which method comprises providing in such body of water using a 1,3-dibromo-5,5-dialkylhydantoin microbiocidal agent described herein (DBDAH), most preferably 1,3-dibromo-5, 5-dimethylhydantoin (DBDMH), a concentration of "free chlorine" that is greater than could be predicted from the concentration of "free chlorine" provided by an equimolar amount of N,N'-bromochloro-5,5-dimethylhydantoin (BCDMH), as determinable by comparative testing for "free chlorine" using Hach Method 8021 (copyright 1997, by Hach Company) and for "total chlorine" using Hach Method 8167 (copyright 1997, by Hach Company), and converting the mg/L $Cl_2$ "free chlorine" values from the tests to percentages of the mg/L $Cl_2$ "total chlorine" values from the tests, the four water samples used in said tests each having the same pH as said body of water and containing an equimolar quantity of BCDMH or DBDAH.

B) A method of A) above wherein the molar amount of the 1,3-dibromo-5,5-dialkylhydantoin microbiocidal agent (DBDAH), most preferably 1,3-dibromo-5,5-dimethylhydantoin, provided in said body of water is less than the molar amount of N,N'-bromochloro-5,5-dimethylhydantoin required to achieve the same degree of microbiological control.

C) Individual methods of A) or B) above wherein the 1,3-dibromo-5,5-dialkylhydantoin microbiocidal agent (DBDAH) used is 1,3-dibromo-5,5-dimethylhydantoin having (a) an average particle size in the range of about 20 to about 600 microns, (b) an average particle size of at least about 175 microns, (c) an average particle size of at least about 200 microns, (d) an average particle size of at least about 300 microns, or (e) an average particle size of at least about 400 microns.

D) Individual methods of A) or B) above wherein the 1,3-dibromo-5,5-dialkylhydantoin microbiocidal agent (DBDAH) used is (i) 1,3-dibromo-5,5-dimethylhydantoin in the form of a compacted product produced without a binder, or (ii) at least one 1,3-dibromo-5,5-dialkylhydantoin microbiocidal agent described herein (DBDAH), most preferably 1,3-dibromo-5,5-dimethylhydantoin, in the form of a compacted product produced using as a binder an amount of a micronized synthetic polyolefin-based hydrocarbon wax and/or a micronized synthetic polyfluorocarbon wax effective to form the compacted product, the wax being compatible with the 1,3-dibromo-5,5-dialkylhydantoin, or (iii) is in the form of a compacted product formed from at least one 1,3-dibromo-5,5-dialkylhydantoin microbiocidal agent described herein (DBDAH), most preferably 1,3-dibromo-5,5-dimethylhydantoin, wherein the compacted product was produced using as a binder an amount of a saturated, normally solid, fatty amide effective to form the compacted product.

E) Individual methods of (i) of D) above wherein the 1,3-dibromo-5,5-dimethylhydantoin being used has an average particle size of at least about 175, at least about 200, at least about 300, or at least about 400, microns.

F) Individual methods of (ii) of D) above wherein the wax is micronized polyethylene wax having, prior to compaction, an average particle size of no greater than about 15 microns, a maximum particle size of no greater than about 40 microns, and a density in the range of about 0.9 to about 1.4 grams per cc at 25° C.; or a micronized polyethylene wax that, prior to compaction, melts at a temperature in the range of about 109° C. to about 111° C.; or a micronized polypropylene wax having, prior to compaction, an average particle size in the range of about 5.0 to about 7.0 microns, a maximum particle size of about 22 microns, and a density in the range of about 0.9 to about 1.4 grams per cc at 25° C.; a micronized polypropylene wax that melts at a temperature in the range of about 140° C. to about 143° C., that has an average particle size in the range of about 5.0 to about 7.0 microns, and that has a maximum particle size of about 22 microns.

G) Individual methods of (iii) of D) above wherein the 1,3-dibromo-5,5-dialkylhydantoin being used is 1,3-dibromo-5,5-dimethylhydantoin having an average particle size of at least about 200, at least about 300, at least about 400, or at least about 500, microns.

H) Individual methods of A) or B) above wherein the microbiocidal activity in said body of water comprises combating *Escherichia coli* and/or *Enterococcus faecium* in said body of water.

I) A method of purveying a microbiological control agent for use in water in accordance with U.S. Environmental Protection Agency regulations, which method comprises purveying a container of a water control agent comprising at least one 1,3-dibromo-5,5-dialkylhydantoin microbiocidal agent described herein (DBDAH), most preferably 1,3-dibromo-5,5-dimethylhydantoin, the container bearing a label having thereon dosage levels pursuant to requirements promulgated by the U.S. Environmental Protection Agency, and specifying either on said label, or on or in packaging for said container, to the effect that the contents are recommended for use, or are for use, in water treatment, or to the effect that the contents are recommended for use, or are for use, in water having a pH of at least about 8.0.

J) Individual methods of H) or I) above wherein the 1,3-dibromo-5,5-dialkylhydantoin being used in H) or the control agent being used in I) is (i) 1,3-dibromo-5,5-dimethylhydantoin in the form of a compacted product produced without a binder, (ii) at least one 1,3-dibromo-5,5-dialkylhydantoin microbiocidal agent described herein (DBDAH), most preferably 1,3-dibromo-5,5-dimethylhydantoin, in the form of a compacted product produced using as a binder an amount of a micronized synthetic polyolefin-based hydrocarbon wax and/or a micronized synthetic polyfluorocarbon wax effective to form the compacted product, the wax being compatible with the 1,3-dibromo-5,5-dialkylhydantoin, or (iii) at least one 1,3-dibromo-5,5-dialkylhydantoin microbiocidal agent described herein (DBDAH), most preferably 1,3-dibromo-5,5-dimethylhydantoin, in the form of a compacted product formed from the 1,3-dibromo-5,5-dialkylhydantoin wherein the compacted product was produced using as a binder an amount of a saturated, normally solid, fatty amide effective to form the compacted product.

K) Individual methods of (i) of J) above wherein the 1,3-dibromo-5,5-dimethylhydantoin being used has an average particle size of at least about 175, at least about 200, at least about 300, or at least about 400, microns.

L) Individual methods of (ii) of J) above wherein the wax is polyethylene wax having, prior to compaction, an average particle size of no greater than about 15 microns, a maximum particle size of no greater than about 40 microns, and a density in the range of about 0.9 to about 1.4 grams per cc at 25° C.; or wherein the wax is a polyethylene wax that, prior to compaction, melts at a temperature in the range of about 109° C. to about 111° C.; or wherein the wax is polypropylene wax having, prior to compaction, an average particle size in the range of about 5.0 to about 7.0 microns, a maximum particle size of about 22 microns, and a density in the range of about 0.9 to about 1.4 grams per cc at 25° C.; or wherein the wax, prior to compaction, is a polypropylene wax that melts at a temperature in the range of about 140° C. to about 143° C., that has an average particle size in the range of about 5.0 to about 7.0 microns, and that has a maximum particle size of about 22 microns.

M) Individual methods of (iii) of J) above wherein the 1,3-dibromo-5,5-dialkylhydantoin used in forming the compacted product is 1,3-dibromo-5,5-dimethylhydantoin having an average particle size of at least about 200, at least about 300, or at least about 400, microns.

N) Individual methods of any of A)–M) above wherein the body of water being treated is industrial cooling water, wastewater, or process water.

O) A method of N) above wherein the treatment of the water comprises passing a sidestream of the water through a bed of the 1,3-dibromo-5,5-dialkylhydantoin such that a biocidally effective amount of the 1,3-dibromo-5,5-dialkylhydantoin is delivered to the water.

P) Individual methods of I) above wherein the microbiological control agent is purveyed for use in at least cooling water, wastewater, or process water.

Q) Individual methods of A) or B) above wherein the microbiocidal activity in said body of water comprises eradicating, substantially eradicating, or reducing biofilm on a surface in contact with said body of water.

R) Individual methods of Q) above wherein the 1,3-dibromo-5,5-dialkylhydantoin being used is 1,3-dibromo-5,5-dimethylhydantoin having (a) an average particle size in the range of about 20 to about 600 microns, (b) an average particle size of at least about 175 microns, (c) an average particle size of at least about 200 microns, (d) an average particle size of at least about 300 microns, or (e) an average particle size of at least about 400 microns.

S) Individual methods of Q) above wherein the 1,3-dibromo-5,5-dialkylhydantoin being used is (i) 1,3-dibromo-5,5-dimethylhydantoin in the form of a compacted product produced without a binder, or (ii) at least one 1,3-dibromo-5,5-dialkylhydantoin described herein (DBDAH), most preferably 1,3-dibromo-5,5-dimethylhydantoin, in the form of a compacted product produced using as a binder an amount of a micronized synthetic polyolefin-based hydrocarbon wax and/or a micronized synthetic polyfluorocarbon wax effective to form the compacted product, the wax being compatible with the 1,3-dibromo-5,5-dialkylhydantoin, or (iii) at least one 1,3-dibromo-5,5-dialkylhydantoin described herein (DBDAH), most preferably 1,3-dibromo-5,5-dimethylhydantoin, in the form of a compacted product formed from the 1,3-dibromo-5,5-dialkylhydantoin wherein the compacted product was produced using as a binder an amount of a saturated, normally solid, fatty amide effective to form the compacted product.

T) Individual methods of (i) of S) above wherein the 1,3-dibromo-5,5-dimethylhydantoin being used has an average particle size of at least about 175, at least about 200, at least about 300, or at least about 400, microns.

U) Individual methods of (ii) of S) above wherein the wax is micronized polyethylene wax having, prior to compaction, an average particle size of no greater than about 15 microns, a maximum particle size of no greater than about 40 microns, and a density in the range of about 0.9 to about 1.4 grams per cc at 25° C.; or a micronized polyethylene wax that, prior to compaction, melts at a temperature in the range of about 109° C. to about 111° C.; or a micronized polypropylene wax having, prior to compaction, an average particle size in the range of about 5.0 to about 7.0 microns, a maximum particle size of about 22 microns, and a density in the range of about 0.9 to about 1.4 grams per cc at 25° C.; a micronized polypropylene wax that melts at a temperature in the range of about 140° C. to about 143° C., that has an average particle size in the range of about 5.0 to about 7.0 microns, and that has a maximum particle size of about 22 microns.

V) Individual methods of (iii) of S) above wherein the 1,3-dibromo-5,5-dialkylhydantoin being used is 1,3-dibromo-5,5-dimethylhydantoin having an average particle size of at least about 200, at least about 300, at least about 400, or at least about 500, microns.

W) Individual methods of A) or B) above wherein the microbiocidal activity in said body of water comprises eradicating, substantially eradicating, or at least reducing *Pseudomonas aeruginosa* biofilm on a surface in contact with said body of water.

X) A method of purveying a biofilm control agent for use in water in accordance with U. S. Environmental Protection Agency regulations, which method comprises purveying a container of a biofilm control agent for use in aqueous media, such agent comprising at least one 1,3-dibromo-5,5-dialkylhydantoin described herein (DBDAH), most preferably 1,3-dibromo-5,5-dimethylhydantoin, the container bearing a label having thereon dosage levels pursuant to requirements promulgated by the U.S. Environmental Protection Agency, and specifying either on said label, or on or in packaging for said container, to the effect that the contents are recommended for use, or are for use, with water having a pH of at least about 8.0.

References herein to biofilm on a surface in contact with an aqueous medium or water, are not to be construed as requiring the aqueous medium or water to be in constant contact with such surface. As long as the aqueous medium or water comes into contact with a surface often enough to result in the formation of biofilm on such surface, it is within the scope of this invention to treat such aqueous medium or water pursuant to this invention so as to combat such biofilm. For example, this invention includes treatment of aqueous media or water that is splashed, sprayed, or dripped on or against a surface with sufficient frequency for biofilm to develop on such surface. It is also to be understood that the aqueous medium or the water can contain any of a variety of contaminants and/or impurities. The only requirements are that such aqueous medium or water periodically or constantly contacts a surface such that the formation of biofilm occurs on the surface, and that the contaminants and/or impurities in the aqueous medium or water do not prevent the 1,3-dibromo-5,5-dialkylhydantoin(s) such as 1,3-dibromo-5,5-dimethylhydantoin, from eradicating, or at least reducing the amount of, the biofilm on such surface.

As used herein, including the claims, the term "purveying" means carrying out or causing to be carried out one or more of the following activities: advertising, marketing, promoting for sale, offering for sale, selling, bartering, trading, leasing, merchandising, importing, exporting, dealing in commerce with, supplying, distributing, delivering, and any and all other activities of similar import.

As used herein, including the claims, the terms "aqueous medium" and "water" refer to and include any liquid in which the predominate liquid component is water. Such aqueous medium or water may contain various other materials, whether organic or inorganic, or both, and is exemplified by recreational water, industrial cooling water, process water and wastewater. As is well known in the art, if the water has a pH of at least about 8, it is not included in the category of recreational water, at least at the present time in the United States.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

It will also be understood that the terms "substantial" and "substantially" denote that chemical operations or treatments ordinarily do not involve absolutes. Thus instead of describing a variable or a result as an absolute, it is far more realistic to describe the variable or result as being in the substantial vicinity of the expressed variable or result. For example when describing eradication of an organism, it can be more realistic to refer to the substantial eradication of the organism rather than to imply that absolute total eradication occurs, since one skilled in the art fully realizes that a substantial kill is a very desirable result, and the possibility always exists that even if a small portion of the organism survives the treatment, the overall result is nevertheless highly beneficial in most cases. Thus this document should be read with the application of common sense.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method of providing microbiological control in an aqueous medium and/or eradication or reduction of biofilm on a surface in contact with such aqueous medium, which method comprises introducing into the aqueous medium a microbiocidally effective amount of at least one 1,3-dibromo-5,5-dialkylhydantoin in which one of the alkyl groups in the 5-position is a methyl group and in which the other alkyl group in the 5-position has in the range of 1 to 4 carbon atoms, wherein (i) the molar quantity of said at least one 1,3-dibromo-5,5-dialkylhydantoin introduced into said aqueous medium is less than the molar quantity of N,N'-bromochloro-5,5-dimethylhydantoin that would be required to effect the same degree of microbiological control in said medium, (ii) the quantity of said at least one 1,3-dibromo-5,5-dialkylhydantoin introduced into said aqueous medium releases an amount of "free chlorine" that is greater than the amount of "free chlorine" that would be released in said medium by an equimolar quantity of N,N'-bromochloro-5,5-dimethylhydantoin, and (iii) the amount of "free chlorine" released by the quantity of said at least one 1,3-dibromo-5,5-dialkylhydantoin introduced into said medium is greater than the amount of "free chlorine" that could be predicted to he released by that quantity of said at least one 1,3-dibromo-5,5-dialkylhydantoin on the basis of the amount of "free chlorine" that would be released in said medium by an equimolar quantity of N,N'-bromochloro-5,5-dimethylhydantoin.

2. A method of claim 1 wherein said at least one 1,3-dibromo-5,5-dialkylhydantoin is 1,3-dibromo-5-isobutyl-5-methylhydantoin.

3. A method of claim 1 wherein said at least one 1,3-dibromo-5,5-dialkylhydantoin is 1,3-dibromo-5-n-propyl-5-methylhydantoin.

4. A method of claim 1 wherein said at least one 1,3-dibromo-5,5-dialkylhydantoin is 1,3-dibromo-5-ethyl-5-methylhydantoin.

5. A method of claim 1 wherein said at least one 1,3-dibromo-5,5-dialkylhydantoin is a mixture of two or more of said 1,3-dibromo-5,5-dialkylhydantoins.

6. A method of claim 1 wherein said at least one 1,3-dibromo-5,5-dialkylhydantoin is a mixture of 1,3-dibromo-5,5-dimethylhydantoin and 1,3-dibromo-5-ethyl-5-methylhydantoin.

7. A method of claim 1 wherein said aqueous medium has a pH of at least about 8.0.

8. A method of providing microbiological control in an aqueous medium having a pH of at least about 8.0 and/or eradication or reduction of biofilm on a surface in contact with such aqueous medium, which method comprises introducing a microbiocidally effective amount of 1,3-dibromo-5,5-dimethylhydantoin into the aqueous medium, wherein (i) the quantity by weight of 1,3-dibromo-5,5-dimethylhydantoin introduced into the aqueous medium is less than the quantity by weight of N,N'-bromochloro-5,5-dimethylhydantoin that would be required to effect the same degree of microbiological control in said medium, (ii) the quantity of 1,3-dibromo-5,5-dimethylhydantoin introduced into the aqueous medium releases an amount of "free chlorine" that is greater than the amount of "free chlorine" that would be released in said medium by an equimolar quantity of N,N'-bromochloro-5,5-dimethylhydantoin, and (iii) the amount of "free chlorine" released by the quantity of the 1,3-dibromo-5,5-dimethylhydantoin introduced into said medium is greater than the amount of "free chlorine" that could be predicted to be released by that quantity of 1,3-dibromo-5,5-dimethylhydantoin on the basis of the amount of "free chlorine" that would be released in said medium by an equimolar quantity of N,N'-bromochloro-5,5-dimethylhydantoin.

9. A method of claim 8 wherein the 1,3-dibromo-5,5-dimethylhydantoin being used has an average particle size of at least about 175 microns.

10. A method of claim 8 wherein the 1,3-dibromo-5,5-dimethylhydantoin being used has an average particle size of at least about 200 microns.

11. A method of claim 8 wherein the 1,3-dibromo-5,5-dimethylhydantoin being used has an average particle size of at least about 300 microns.

12. A method of claim 8 wherein the 1,3-dibromo-5,5-dimethylhydantoin being used is in the form of a shape-retentive pressure compacted article produced by pressure compacting 1,3-dibromo-5,5-dimethylhydantoin particulate solids without use of a binder and without prior treatment of such solids to enhance their compactibility.

13. A method of claim 12 wherein the 1,3-dibromo-5,5-dimethylhydantoin particulate solids used in forming said article had, prior to compaction, an average particle size of at least about 175 microns.

14. A method of claim 8 wherein the 1,3-dibromo-5,5-dimethylhydantoin being used is in the form of a shape-retentive pressure compacted article produced by pressure compacting 1,3-dibromo-5,5-dimethylhydantoin particulate solids with use of a binder.

15. A method of claim 14 wherein the 1,3-dibromo-5,5-dimethylhydantoin particulate solids used in forming said article had, prior to compaction, an average particle size of at least about 175 microns.

16. A method of claim 8 wherein the 1,3-dibromo-5,5-dimethylhydantoin being used is in the form of a compacted product produced using as a binder an amount of a micronized synthetic polyolefin-based hydrocarbon wax and/or a micronized synthetic polyfluorocarbon wax effective to form said compacted product, said wax being compatible with said 1,3-dibromo-5,5-dimethylhydantoin.

17. A method of claim 16 wherein said wax is polyethylene wax having, prior to compaction, an average particle size of no greater than about 15 microns, a maximum particle size of no greater than about 40 microns, and a density in the range of about 0.9 to about 1.4 grams per cc at 25° C.

18. A method of claim 16 wherein said wax is a polyethylene wax that melts at a temperature in the range of about 109° C. to about 111° C.

19. A method of claim 16 wherein said wax is polypropylene wax having, prior to compaction, an average particle size in the range of about 5.0 to about 7.0 microns, a maximum particle size of about 22 microns, and a density in the range of about 0.9 to about 1.4 grams per cc at 25° C.

20. A method of claim 16 wherein said wax is a polypropylene wax that melts at a temperature in the range of about 140° C. to about 143° C., that prior to compaction has an average particle size in the range of about 5.0 to about 7.0 microns, and that prior to compaction has a maximum particle size of about 22 microns.

21. A method of claim 8 wherein the 1,3-dibromo-5,5-dimethylhydantoin being used is in the form of a compacted product formed from 1,3-dibromo-5,5-dimethylhydantoin having an average particle size of at least 175 microns, and wherein said compacted product was produced using as a binder an amount of a saturated, normally solid, fatty amide effective to form said compacted product.

22. A method of claim 21 wherein the 1,3-dibromo-5,5-dimethylhydantoin used in forming said compacted product had an average particle size of at least about 200 microns.

23. A method of claim 21 wherein the 1,3-dibromo-5,5-dimethylhydantoin used in forming said compacted product had an average particle size of at least about 300 microns.

24. A method of effecting microbiocidal activity in water having a pH of at least about 8.0, which method comprises providing in such water using a 1,3-dibromo-5,5-dimethylhydantoin microbiocidal agent, a microbiocidally effective amount of "free chlorine" that is greater than could be predicted from the amount of "free chlorine" that would be released in said water by an equimolar quantity of N,N'-bromochloro-5,5-dimethylhydantoin, while using a smaller quantity by weight of 1,3-dibromo-5,5-dimethylhydantoin than the quantity by weight of N,N'-bromochloro-5,5-dimethylhydantoin that would be required to release in said water the same microbiocidally effective amount of "free chlorine", wherein the 1,3-dibromo-5,5-dimethylhydantoin being used is in the form of a compacted product produced using as a binder an amount of a micronized synthetic polyethylene wax effective to form said compacted product, said wax having, prior to compaction, an average particle size of no greater than about 15 microns, a maximum particle size of no greater than about 40 microns, and a density in the range of about 0.9 to about 1.4 grams per cc at 25° C., said wax being compatible with said 1,3-dibromo-5,5-dimethylhydantoin.

25. A method of claim 24 wherein said polyethylene wax melts at a temperature in the range of about 109° C. to about 111° C.

26. A method of effecting microbiocidal activity in water having a pH of at least about 8.0, which method comprises providing in such water using a 1,3-dibromo-5,5-dimethylhydantoin microbiocidal agent, a microbiocidally effective amount of "free chlorine" that is greater than could be predicted from the amount of "free chlorine" that would be released in said water by an equimolar quantity of N,N'-bromochloro-5,5-dimethylhydantoin, while using a smaller quantity by weight of 1,3-dibromo-5,5-dimethylhydantoin than the quantity by weight of N,N'-bromochloro-5,5-dimethylhydantoin that would be required to release in said water the same microbiocidally effective amount of "free chlorine", wherein the 1,3-dibromo-5,5-dimethylhydantoin being used is in the form of a compacted product produced using as a binder an amount of a micronized synthetic polypropylene wax effective to form said compacted product, said wax having, prior to compaction, an average particle size in the range of about 5.0 to about 7.0 microns, a maximum particle size of about 22 microns, and a density in the range of about 0.9 to about 1.4 grams per cc at 25° C., said wax being compatible with said 1,3-dibromo-5,5-dimethylhydantoin.

27. A method of effecting microbiocidal activity in water having a pH of at least about 8.0, which method comprises providing in such water using a 1,3-dibromo-5,5-dimethylhydantoin microbiocidal agent, a microbiocidally effective amount of "free chlorine" that is greater than could be predicted from the amount of "free chlorine" that would be released in said water by an equimolar quantity of N,N'-bromochloro-5,5-dimethylhydantoin, while using a smaller quantity by weight of 1,3-dibromo-5,5-dimethylhydantoin than the quantity by weight of N,N'-bromochloro-5,5-dimethylhydantoin that would be required to release in said water the same microbiocidally effective amount of "free chlorine", wherein the 1,3-dibromo-5,5-dimethylhydantoin being used is in the form of a compacted product produced using as a binder an amount of a micronized synthetic wax effective to form said compacted product, wherein said wax is a polypropylene wax that melts at a temperature in the range of about 140° C. to about 143° C., that prior to compaction has an average particle size in the range of about 5.0 to about 7.0 microns, and that prior to compaction has a maximum particle size of about 22 microns, said wax being compatible with said 1,3-dibromo-5,5-dimethylhydantoin.

* * * * *